(12) United States Patent
Flasinski

(10) Patent No.: US 8,940,962 B2
(45) Date of Patent: Jan. 27, 2015

(54) CHIMERIC PROMOTER COMPRISING FMV ENHANCER AND HSP81-2 PROMOTER AND PLANTS TRANSFORMED THEREWITH

(75) Inventor: Stanislaw Flasinski, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 439 days.

(21) Appl. No.: 13/062,694

(22) PCT Filed: Sep. 21, 2009

(86) PCT No.: PCT/US2009/057697
§ 371 (c)(1),
(2), (4) Date: May 24, 2011

(87) PCT Pub. No.: WO2010/033922
PCT Pub. Date: Mar. 25, 2010

(65) Prior Publication Data
US 2011/0225673 A1    Sep. 15, 2011

Related U.S. Application Data

(60) Provisional application No. 61/098,950, filed on Sep. 22, 2008.

(51) Int. Cl.
C12N 15/29    (2006.01)
C12N 15/63    (2006.01)
C12N 15/82    (2006.01)
C12N 15/113   (2010.01)

(52) U.S. Cl.
CPC ........ C12N 15/8225 (2013.01); C12N 15/8261 (2013.01)
USPC .......... 800/279; 800/281; 800/283; 800/284; 800/289; 800/290; 800/298; 800/300; 800/302; 800/305; 800/309; 800/312; 800/314; 800/306; 800/317.3; 800/317.4; 800/318; 800/320.1; 800/320.2; 800/320.3; 800/322; 800/308; 800/319; 800/320; 435/410; 435/418; 435/419; 435/468; 536/24.1

(58) Field of Classification Search
None
See application file for complete search history.

(56) References Cited

U.S. PATENT DOCUMENTS 5,097,025 A    3/1992    Benfey et al.
5,424,200 A    6/1995    McPherson et al.
(Continued)

FOREIGN PATENT DOCUMENTS

WO    WO 2008/081478 A2    7/2008

OTHER PUBLICATIONS

GenBank Accession No. AB011476. *Arabidopsis thaliana* genomic DNA, chromosome 5, P1 clone: MDA7. published Feb. 14, 2004. pp. 1-24.*

(Continued)

*Primary Examiner* — Brent T Page
*Assistant Examiner* — Ashley K Buran
(74) *Attorney, Agent, or Firm* — Dentons US LLP; Carine M. Doyle Esq.

(57) ABSTRACT

The present invention provides novel promoters for use in plants. Specifically, the present invention provides novel chimeric promoters comprising combinations of plant viral enhancer elements and plant promoters. The present invention also provides DNA constructs; transgenic cells, plants, and seeds containing these novel chimeric promoters; and methods for preparing and using the same.

16 Claims, 11 Drawing Sheets

(56) References Cited

U.S. PATENT DOCUMENTS

| | | | |
|---|---|---|---|
| 6,051,753 A | 4/2000 | Comai et al. | |
| 6,660,911 B2 * | 12/2003 | Fincher et al. | 800/300 |
| 6,949,696 B2 | 9/2005 | Fincher et al. | |
| 7,371,848 B2 | 5/2008 | Conner et al. | |
| 2002/0144304 A1 * | 10/2002 | Fincher et al. | 800/278 |
| 2012/0084885 A1 * | 4/2012 | Alexandrov et al. | 800/298 |

OTHER PUBLICATIONS

Yabe et al. Analysis of tissue-specific expression of *Arabidopsis thaliana* HSP90-family gene HSP81. Plant Cell and Physiology. 1994. 35(8): 1207-1219.*

Omirulleh et al., "Activity of a chimeric promoter with the doubled CaMV 35S enhancer element in protoplast-derived cells and transgenic plants in maize," *Plant Molecular Biology*, 21(3):415-428, 1993.

Comai et al., "Novel and useful properties of a chimeric plant promoter combining CaMV 35S and MAS elements," *Plant Molecular Biology*, 15(1):373-382, 1990.

Kim et al., "A 20 nucleotide upstream element is essential for the nopaline synthase (nos) promoter activity," *Plant Molecular Biology*, 24:105-117, 1994.

Benfey et al., "The CaMV 35S enhancer contains at least two domains which can confer different developmental and tissue-specific expression patterns," *The EMBO Journal*, 8(8):2195-2202, 1989.

Odell et al., "Identification of DNA sequences required for activity of the cauliflower mosaic virus 35S promoter," *Nature*, 313:810-812, 1985.

Cho et al., "Regulation of root hair initiation and expansin gene expression in arabidopsis," *The Plant Cell*, 14:3237-3253, 2002.

Piechulla et al., "Identification of tomato Lhc promoter regions necessary for circadian expression," *Plant Molecular Biology*, 38:655-662, 1998.

Welsch et al., "Structural and functional characterization of the phytoene synthase promoter from *Arabidopsis thaliana*," *Planta*, 216:523-534, 2003.

* cited by examiner

SEQUENCE LISTING

```
<160> NUMBER OF SEQ ID NOS: 22

<210> SEQ ID NO 1
<211> LENGTH: 824
<212> TYPE: DNA
<213> ORGANISM: Artificial sequence
<220> FEATURE:
<223> OTHER INFORMATION: Linkage of a plant promoter and viral enhancer
      element

<400> SEQUENCE: 1
ggaagtttct ctcttgaggg aggttgctcg tggaatggga cacatatggt tgttataata      60
aaccatttcc attgtcatga gattttgagg ttaatatata ctttacttgt tcattatttt     120
atttggtgtt tgaataaatg atataaatgg ctcttgataa tctgcattca ttgagatatc     180
```

```
aaatatttac tctagagaag agtgtcatat agattgatgg tccacaatca atgaaatttt    240
tgggagacga acatgtataa ccatttgctt gaataacctt aattaaaagg tgtgattaaa    300
tgatgtttgt aacatgtagt actaaacatt cataaaacac aaccaaccca agaggtattg    360
agtattcacg gctaaacagg ggcataatgg taatttaaag aatgatatta ttttatgtta    420
aaccctaagc ttcgaaggat agtgggattg tgcgtcatcc cttacgtcag tggagatatc    480
acatcaatcc acttgctttg aagacgtggt tggaacgtct tcttttccca cgatgctcct    540
cgtgggtggg ggtccatctt tgggaccact gtcggcagag gcatcttcaa cgatgaggcc    600
tcgaaggata gtgggattgt gcgtcatccc ttacgtcagt ggagatatca catcaatcca    660
cttgctttga agacgtggtt ggaacgtctt cttttccac gatgctcctc gtgggtgggg    720
gtccatcttt gggaccactg tcggcagagg catcttcaac gatgaggcct aagcttggtt    780
tcggattcaa cgctataaat aaaaccactc tcgttgctga ttcc                    824

<210> SEQ ID NO 2
<211> LENGTH: 1633
<212> TYPE: DNA
<213> ORGANISM: Artificial sequence
<220> FEATURE:
<223> OTHER INFORMATION: Linkage of a plant promoter and viral enhancer
      element

<400> SEQUENCE: 2
aattctcagt ccaaagcctc aacaaggtca gggtacagag tctccaaacc attagccaaa     60
agctacagga gatcaatgaa gaatcttcaa tcaaagtaaa ctactgttcc agcacatgca    120
tcatggtcag taagtttcag aaaaagacat ccaccgaaga cttaaagtta gtgggcatct    180
ttgaaagtaa tcttgtcaac atcgagcagc tggcttgtgg ggaccagaca aaaaaggaat    240
ggtgcagaat tgttaggcgc acctaccaaa agcatctttg cctttattgc aaagataaag    300
cagattcctc tagtacaagt ggggaacaaa ataacgtgga aaagagctgt cctgacagcc    360
cactcactaa tgcgtatgac gaacgcagtg acgaccacaa agaattagc ttgagctcag    420 gatttagcag cattccagat tgggttcaat caacaaggta cgagccatat cactttattc    480
aaattggtat cgccaaaacc aagaaggaac tcccatcctc aaaggtttgt aaggaagaat    540
tcgataaaca tgactctctt aaggtagcca agcccggga tcatgtatat ttgtgcatat    600
ccatgaaaat ttgtgttata tatcgatat ataatgtgat acacataggc gtccataaaa    660
gaattgtgtt gtatacacga tatacaaagt gatatacaga tgtccttaaa aatatgtgtg    720
tgatatacat tgatgtacac aatatgcaac gcgatataca catgtcacag ttggatttta    780
ggtctgatgt tttacatgaa atcagtctaa atcacttcta atcttgctca aattttgtat    840
atagccccgt ttaggtattt tcaaccaatt tcactcacac cactcgttca atctaaccaa    900 aaaaagaag agagaagaaa acaaagttg aaatgaattt ttctctctta gtttttgctt    960 ataattttc tgattacctt ttcaccccac tgatttttt tgcataattt gcaaggattt   1020 ttgctaaaact atgagagcga agaaaagag atagaagaag aaatacaagg agagaaaggg   1080
ggagggacgc agtgaacaaa aaaagaagtt agcggcgaag agggggggg ggggaagca    1140 gacggtttgg ggccaattgt tgagagaga atatataaga gagtagtttt tttaggattt   1200
ggctatataa tgtcaatttt ttggggctat cttttcctaa cctaatataa gactaaaaaa   1260
ttgtcaattc ctgttatgtg ttatcacctg gtgccatttt ctcatagtta tacatatagt   1320
gaaaggaaaa gagggtatta gtgccaattt tgtaaagagg ttagacctaa attaggccca   1380
```

```
agaggcccaa tagaaaatct agccctcaat tttgtggaat ccacgtcacc gacttcttgc    1440
attaccaccc gaagcggctc cgtattgatc ctgtaactcc caatttcggg tcaaaatagg    1500
aatttcaaat acagaagcca aaaaaaaaag gaaagtaatc caaaacagta ttcagaaaga    1560
ccataaaaaa acactagtct caatcttttct cttttcctct ttcctgaact cctgcggcgt    1620
agatccgagg agt                                                       1633

<210> SEQ ID NO 3
<211> LENGTH: 1610
<212> TYPE: DNA
<213> ORGANISM: Artificial sequence
<220> FEATURE:
<223> OTHER INFORMATION: Linkage of a plant promoter and viral enhancer
      element

<400> SEQUENCE: 3
ggtccgattg agacttttca acaaagggta atatccggaa acctcctcgg attccattgc      60
ccagctatct gtcactttat tgtgaagata gtggaaaagg aaggtggctc ctacaaatgc     120
catcattgcg ataaaggaaa ggccatcgtt gaagatgcct ctgccgacag tggtcccaaa     180
gatggacccc cacccacgag gagcatcgtg aaaaagaag acgttccaac cacgtcttca     240
aagcaagtgg attgatgtga tggtccgatt gagacttttc aacaaagggt aatatccgga     300
aacctcctcg gattccattg cccagctatc tgtcacttta ttgtgaagat agtggaaaag     360
gaaggtggct cctacaaatg ccatcattgc gataaaggaa aggccatcgt tgaagatgcc     420
tctgccgaca gtggtcccaa agatggaccc ccacccacga ggagcatcgt ggaaaaagaa     480
gacgttccaa ccacgtcttc aaagcaagtg gattgatgtg ataaacatga ctctcttaag     540
gtagccaaag cccgggatca tgtatatttg tgcatatcca tgaaaatttg tgttatatat     600
acgatatata atgtgataca cataggcgtc cataaaagaa ttgtgttgta tacgcgatat     660
acaaagtgat atacagatgt ccttaaaaat atgtgtgtga tatacattga tgtacacaat     720
atgcaacgcg atatacacat gtcacagttg gattttaggt ctgatgtttt acatgaaatc     780
agtctaaatc acttctaatc ttgctcaaat tttgtatata gccccgttta ggtattttca     840
accaatttca ctcacaccac tcgttcaatc taaccaaaaa aagaagagaa gagaaaaac     900 aaagttgaaa tgaattttc tctcttagtt tttgcttata atttttctga ttacctttttc     960 accccactga tttttttgc ataatttgca aggattttg ctaaactatg agagcgaaag     1020
aaaagagata gaagaagaaa tacaaggaga gaaaggggga gggacgcagt gaacaaaaaa     1080
agaagttagc ggcgaagagg gggggggggg ggaagcagac ggtttggggc caattgtttg     1140
agagagaata tataagagag tagtttttttt aggatttggc tatataatgt caatttttttg    1200 gggctatctt ttcctaacct aatataagac taaaaaaattg tcaattcctg ttatgtgtta     1260
tcacctggtg ccattttctc atagttatac atatagtgaa aggaaaagag ggtattagtg    1320
ccaattttgt aaagaggtta gacctaaatt aggcccaaga ggcccaatag aaaatctagc    1380
cctcaatttt gtggaatcca cgtcaccgac ttcttgcatt accacccgaa gcggctccgt    1440
attgatcctg taactcccaa tttcgggtca aataggaat ttcaaataca gaagccaaaa    1500 aaaaaggaa agtaatccaa aacagtattc agaaagacca taaaaaaaca ctagtctcaa    1560 tcttttctctt ttcctctttc ctgaactcct gcggcgtaga tccgaggagt               1610

<210> SEQ ID NO 4
<211> LENGTH: 2132
```

```
<212> TYPE: DNA
<213> ORGANISM: Artificial sequence
<220> FEATURE:
<223> OTHER INFORMATION: Linkage of a plant promoter and viral enhancer
      element

<400> SEQUENCE: 4
aattctcagt ccaaagcctc aacaaggtct gggtacagag tctccaaacc attagccaaa      60
agctacagga gatcaatgaa gaatcttcaa tcaaagtaaa ctactgttcc agcacatgca     120
tcatggtcag taagtttcag aaaaagacat ccaccgaaga cttaaagtta gtgggcatct     180
ttgaaagtaa tcttgtcaac atcgagcagc tggcttgtgg ggaccagaca aaaaaggaat     240
ggtgcagaat tgttaggcgc acctaccaaa agcatctttg cctttattgc aaagataaag     300
cagattcctc tagtacaagt ggggaacaaa ataacgtgga aaagagctgt cctgacagcc     360
cactcactaa tgcgtatgac gaacgcagtg acgaccacaa agaattagc ttgagctcag      420
gatttagcag cattccagat tgggttcaat caacaaggta cgagccatat cactttattc     480
aaattggtat cgccaaaacc aagaaggaac tcccatcctg cagggaattc ctttaaatat     540
tccttttata ctaaatatgg caactgaata ttattttta acgaatcaaa aattaaaaaa      600
caaatctata cacctctat acataaaatt gcatccacca aatgctacta tctataaact      660
aaacattgat gggtcttgct catctaccca gcaaaatatg gtattggtgg agttttcga      720
aactaccaag gcaactggat catgagattt gcaggtaaat ccaatccagg cgcaaatgtt     780
cagacagaac tccttgcact actcatggga ttgaaacttg ctgtgcaaca atatctcaac     840
cccatcatca ttgagacaga tgcacatgca atcatcggta tgtttaactc aactactatg     900
cactacacta atctcattaa cgattgcagg ttattactcc tacagctgga tagccctcct     960
atacaataca tctacaaagg gcaaaattgt gttgcagata gtttagccaa acatgaagtc    1020
atgcatgcac aggagagctg catactttgt gggagaccat catcttttgc agagccttct    1080
taccaccaag atcatatcga cacgctacaa aggaggttcg ttacaatcaa ctccagtaac    1140
tcaacacaac cgctctttgc tctaactact ttgtgtaata gtattgttct atctagtact    1200
aatagtagtg ttctatctag tactaactat ctttcttgta atgattccca tacgggggtc    1260
tttgtagtaa actctagctt agtaactatg atgcctctta tgtatcttgt aaactgttct    1320
catgtacctg gttaattccc tataatataa gtacatcttt tcgacaaaaa agaagaagaa    1380
acaacaacat tttagcaatg aaaaataaga agacaaacac aacacattta tagaattaac    1440
atttgaacaa tgactagtgg tgcagctagt tggtgcatta ccctctttgc cccctccccc    1500
gcgcataaaa aaatctaaaa aataatatca gtaaaaagaa agaaaaaaac aaaggaagt    1560
gtgaaaagtg aaaagactgc tttcgtttta tttatacttt cacacaaaca agccacaaga    1620
atcaatcata atatattaaa atctgcaaca ctcttaaagc atgcactcct gcagggtttg    1680
taaggaagaa ttctcagtcc aaagcctcaa caaggtcagg gtacagagtc tccaaaccat    1740
tagccaaaag ctacaggaga tcaatgaaga atcttcaatc aaagtaaact actgttccag    1800
cacatgcatc atggtcagta agtttcagaa aaagacatcc accgaagact taaagttagt    1860
gggcatcttt gaaagtaatc ttgtcaacat cgagcagctg gcttgtgggg accagacaaa    1920
aaaggaatgg tgcagaattg ttaggcgcac ctaccaaaag catctttgcc tttattgcaa    1980
agataaagca gattcctcta gtacaagtgg ggaacaaaat aacgtggaaa agagctgtcc    2040
tgacagccca ctcactaatg cgtatgacga acgcagtgac gaccacaaaa gaattccctc    2100
tatataagaa ggcattcatt cccatttgaa gg                                 2132
```

<210> SEQ ID NO 5
<211> LENGTH: 2821
<212> TYPE: DNA
<213> ORGANISM: Artificial sequence
<220> FEATURE:
<223> OTHER INFORMATION: Linkage of a plant promoter and viral enhancer element

<400> SEQUENCE: 5

```
atcaagcttc tgcaggtcct gctcgagtgg aagctaattc tcagtccaaa gcctcaacaa      60
ggtcagggta cagagtctcc aaaccattag ccaaaagcta caggagatca atgaagaatc     120
ttcaatcaaa gtaaactact gttccagcac atgcatcatg gtcagtaagt ttcagaaaaa     180
gacatccacc gaagacttaa agttagtggg catctttgaa agtaatcttg tcaacatcga     240
gcagctggct tgtggggacc agacaaaaaa ggaatggtgc agaattgtta ggcgcaccta     300
ccaaaagcat cttttgccttt attgcaaaga taaagcagat tcctctagta caagtgggga     360
acaaaataac gtggaaaaga gctgtcctga cagcccactc actaatgcgt atgacgaacg     420
cagtgacgac cacaaaagaa ttagcttgcc tgcaggaatt ctgatgtctc aaatcaagca     480
tatttttctg gaacttctgg gaaaggaaat ggtgatcttc gtgttgaaaa ccctttagtt     540
ggtttagttc ctagaaacac tggttcgctt tcgagttctt tagcagcgga aaggcaaaga     600
tacgtggagc attttggcta tagctcaaaa aaaggtcata agttatctgt agaatctgat     660
cttcaagttg aggtttctga aattggatca cctcccacta cagttgatgg gaataattct     720
tctgatgaag aaaaatcacg tattgtcaac gaatcagaca ttgggaagga cgggatttt     780
agtggtgagg agagcattgt ggatagaact gaagaaactc aaatgttacc agtggagaaa     840
gttgataaag atttaaatga aacgatttct aaggtctctc cagaaactta tgtagccaaa     900
caagttgagg gtctgtctga tggtactgat atcaacggaa gatctgagga agaagagagc     960
tcaaaatccg gacgctttcc actggaaaat tcagacaaag gattctatat acatgaagag    1020
tcaacagttc ctcacatcaa tgaagttatt tcgagaagag aagaggttat atagttcttg    1080
ttcttgtcag gttttatgga aatatgattg ctacttgcaa tgtgtttctc aaaatgttga    1140
atttgaatat attccttgta ccgttatgac aggaacgtgt ccaaaacttg actgatgaga    1200
tgaagataaa tgatgactct gatgaacctg aagcctttga agaagaaca aatcaagaac    1260
cccaagaaca ttttggggga aatgatggag accaatcaac tcaagagttg caagaacttg    1320
tggaacctga agtttcaaat gtgaacaatg tcacatcaga cgagtctgct acttccccaa    1380
gatcagtgtt accagacatg ttgttatctt tagaccagac ttatactctg acttctgaga    1440
gtttggaaca tacattagat agtcaacctc cgccagtgat tccatatccg gaatctccac    1500
agaatcaatc aggtgttgat gggaacagta gatgaagtgt gctcagagat cagtttcaat    1560
gacagtactt gaactgaaat gtacctttaa caaaatgatg acgtgtgttt tctaaaacaa    1620
ggatagtctg aggcaagtga gaagctagag aagaagtttc ttctttagat gccattgtcc    1680
ttttgttgaa cactcaacaa attcaggctt atgcagtgta gaggatttag gttccctagc    1740
taaattttat gtatatgcta aagttgaaca ttaatgtgtg gaatttgatt tagtgaagtg    1800
atcatcattt tgtttgatga taactgagat ataatttatg ttgtcttta aaaagttta    1860
tgtattatag tatgggaaat ctgataatga ttggttattt ctaaatttta gtaaattact    1920
ttctctttta gtttaaaata aataaggat cgttgattat caacaagata aaattttta    1980
caacaacaac aactcttctc ctgattatga agctctaaat atttttaat attaatgacc    2040
```

| | |
|---|---|
| aattaatttt accttttaat ataagtggtc accttttttt tttaaaaccg tatatcaact | 2100 |
| tatctgcgtt tttctcgtat tctctcatgg gattaatatt tgcttttaaa tgtggataaa | 2160 |
| tgatgtccaa aaaacatttt ggataaaatt ttatccatgc tgaaaatgt ataacaagaa | 2220 |
| ttttttttt tttttaata acaaatactt ataattctta cgattatata ggtgtagatt | 2280 |
| attattcttt ttcatgcaat gaccatgcgg ataattttgt ctaaatttta tccaaaactt | 2340 |
| ttttcacact catttcttat aggaaaaata ttctacccag acttgcttgt gtaattatat | 2400 |
| gaatgttaaa aatattacat aatcaaaagc caagctctga gatcatatat gtcgtataaa | 2460 |
| aaattattat tgtgtcgatc aaacgtcatt atctttact taaaaaaaaa agagttttta | 2520 |
| tttcttaatc tcgatattga tctaaacgat ttaattgttt attatttaa atgataatat | 2580 |
| cttaatatca aaacacatat atcttatcag taattatcca catttattct cagataaaac | 2640 |
| aggatcgagt cagaagaaaa attcgttcaa aaagattcag ttgttaaatc ttagtttatc | 2700 |
| caaaaccctc acactcatct ataaaagaaa ccccatctcc tctcttaggc atttgagttt | 2760 |
| tatttacgat cctcaatacc acatagtcag aaatattaaa agaagctaag agatcaacaa | 2820 |
| c | 2821 |

<210> SEQ ID NO 6
<211> LENGTH: 1579
<212> TYPE: DNA
<213> ORGANISM: Artificial sequence
<220> FEATURE:
<223> OTHER INFORMATION: Linkage of a plant promoter and viral enhancer element

<400> SEQUENCE: 6

| | |
|---|---|
| atcaagcttc tgcaggtcct gctcgagtgg aagctaattc tcagtccaaa gcctcaacaa | 60 |
| ggtcagggta cagagtctcc aaaccattag ccaaaagcta caggagatca atgaagaatc | 120 |
| ttcaatcaaa gtaaactact gttccagcac atgcatcatg gtcagtaagt ttcagaaaaa | 180 |
| gacatccacc gaagacttaa agttagtggg catctttgaa agtaatcttg tcaacatcga | 240 |
| gcagctggct tgtggggacc agacaaaaaa ggaatggtgc agaattgtta ggcgcaccta | 300 |
| ccaaaagcat cttgcctttt attgcaaaga taaagcagat tcctctagta caagtgggga | 360 |
| acaaaataac gtggaaaaga gctgtcctga cagcccactc actaatgcgt atgacgaacg | 420 |
| cagtgacgac cacaaaagaa ttagcttgcc tgcatcaagc ttgtgaaaac gtgaaggttt | 480 |
| taaaactcaa atacaagaaa tcacaagata aataaattca tatagactct cagtacatac | 540 |
| ctcagaggtt tttcctatag agtacccatt tggatagagg ctcaatatga aggaaacttc | 600 |
| atgatctgca gagaaaccaa aatgcactca attcaacata gctagaattt agcaaaacat | 660 |
| tatgtgtcaa agtggttcgt tgagatccaa acctggagat atatcgggta aagatggctt | 720 |
| cgaaaacccg gaaacatcgc caatattgct atcatcagtg gcctgaacca aacgtaataa | 780 |
| attttctata taacttttcca aaataagcga atttagttgg aacacaatac aactaaaatt | 840 |
| ctaagttaaa ttacctttgg tttcccagat agaacgattg cttttgggga atcaggagta | 900 |
| gccaattcag tagaaatctt aggtcgaaac tttctaccaa ccttcgatat cttaaacgag | 960 |
| acacccatgg attctctcca gagagatgaa gctcaaacct gtctaggtac tgtcaataaa | 1020 |
| cgatacagaa ataaaaaaga cacgagaatt gaagaaatcg aagaatgaat tttaagaaag | 1080 |
| ctagagaaat tgaaacctta tgagcttgtt acagagaaga tcatcaaaca attggatcgg | 1140 |
| atagaaagcg agagaaatca aaggtgacta agaatagagc aatgaagaat tcataaacat | 1200 |

```
ggaatttgtg aaacacaggt gggaaatttt tgaagaagat gcgatcggaa gagaaaggaa      1260
gagagattat tgttagggtt cttcttctaa cttcaaagta gcagaaaaag aattatcttt      1320
gtgtctctgt gcacacttgg atttcggttt aagacaaaac ggaagttgaa ccagttatta      1380
attttggtta gcttcgatta aaatttgggt aaccgagttt gggggtagaa tagacatttt      1440
gcaaattagg gttttgcttg atatataaaa tccttcaccc ttataagcct ttcgtcgcct      1500
cttcgtgtga tttactgagt gaaaaaagct tatcgcggcg attagttccc ggcgaagaag      1560
aagaagagag ataagaaac                                                  1579

<210> SEQ ID NO 7
<211> LENGTH: 1517
<212> TYPE: DNA
<213> ORGANISM: Artificial sequence
<220> FEATURE:
<223> OTHER INFORMATION: Linkage of a plant promoter and viral enhancer
      element

<400> SEQUENCE: 7
atcaagcttc tgcaggtcct gctcgagtgg aagctaattc tcagtccaaa gcctcaacaa       60
ggtcagggta cagagtctcc aaaccattag ccaaaagcta caggagatca atgaagaatc      120
ttcaatcaaa gtaaactact gttccagcac atgcatcatg gtcagtaagt ttcagaaaaa      180
gacatccacc gaagacttaa agttagtggg catctttgaa agtaatcttg tcaacatcga      240
gcagctggct tgtggggacc agacaaaaaa ggaatggtgc agaattgtta ggcgcaccta      300
ccaaaagcat cttttgcctt tattgcaaga taaagcagat tcctctagta caagtgggga      360
acaaaataac gtggaaaaga gctgtcctga cagcccactc actaatgcgt atgacgaacg      420
cagtgacgac cacaaaagaa ttagcttgcc tgcatcaagc tttcatgaat gcaacactgg      480
aaaatgacaa taacatatat gaatgtagta attacctgtc ctcctgtttc agtctaagaa      540
ctttagccat atgccaaaac tcagagcctt gaacacgaac aactccaccc tataaacaat      600
cataaaacga tttacacaaa gaggagctta tcatttcaaa caacaagaac atttaatatt      660
atcatttcac catgattttta ccagaaattt cttagagatt acagtgaatt acagtaattt      720
ctaaacttct cagtgattac cctcactctc atttcgattg gattcttaca cagatttaaa      780
gggaacaaaa attatatgag ataaagatag agatagatat ggtgtgtgcc ttgcgagatg      840
gaagatcatc ggaaaagaat cgaggaaggc caccgcgaga ttgattccgg agattcaaat      900
ccgacggagg agacgaagat acagtagcaa acgatttgaa gctagaagtc ggaagccatg      960
aacgaacgag actcggcaaa tcggaaaaca gtggccgtga agccgccgct agcgctctca     1020
tcatttactc aaagctttga attttttggtt accattcga agattttggt taatactagt     1080
ttcttatcgt ttcggtttac tttaaatatt ggtctgatcc ggttcaattc taattaaatt     1140
ccggttcatt tccacgcaat tcaaggaatt ttgctatttc aaaaataaag agaaacggtc     1200
agaaagcgat tgccaaacag aatctaagga atcaaaattc aaaattagaa atacgcaaac     1260
tcacgaggat atcaacaaat cgtggttttta acgacaaccc aattacatca ctacacgtgt     1320
atcatacgtg ccgttacata cagatggata ctttcgctta taaatatagc atcaaacagc     1380
tctgtaaaaa cctagaaatc gaaaaaatca gatctagatc taaagaaga gcgtcttcat     1440 aaacgcccct tcttcttctt gtcttcttcc ctgcaaatct agtttctaga tctttctttt     1500
cttccgcgaa acgaaac                                                    1517
```

<210> SEQ ID NO 8
<211> LENGTH: 1399
<212> TYPE: DNA
<213> ORGANISM: Artificial sequence
<220> FEATURE:
<223> OTHER INFORMATION: Linkage of a plant promoter and viral enhancer element

<400> SEQUENCE: 8

```
aattctcagt ccaaagcctc aacaaggtca gggtacagag tctccaaacc attagccaaa    60
agctacagga gatcaatgaa gaatcttcaa tcaaagtaaa ctactgttcc agcacatgca   120
tcatggtcag taagtttcag aaaaagacat ccaccgaaga cttaaagtta gtgggcatct   180
ttgaaagtaa tcttgtcaac atcgagcagc tggcttgtgg ggaccagaca aaaaaggaat   240
ggtgcagaat tgttaggcgc acctaccaaa agcatctttg cctttattgc aaagataaag   300
cagattcctc tagtacaagt ggggaacaaa ataacgtgga aaagagctgt cctgacagcc   360
cactcactaa tgcgtatgac gaacgcagtg acgaccacaa agaattagc ttgcctgcag    420
gattagctta gatcgggctt aattaaggcg cgccggccaa gtcggccgcg gccgcaagct   480
tacttgcgac agaaacagct ttgatatatt attactcacc cgttatcgat atggaatata   540
tactttaaga actcactaaa tcatatcctt catgtcggtt taaagattag tcacgtatct   600
gcacattctg taagtatagt aatctcataa aaaacctggt ctctgttctc tgtgaatcca   660
taggttattg cactggcgta ctactgtata tcatatttcc ctggtggatc atcgggaatg   720
aagttcctca gttctactct tacctcctct gtcttccgaa tgtttgggag atgagctttc   780
gctttgacct atgcaagaa ataacttga ttctctcgtg tataaagaaa gatgaaagat     840
cttcaacagt ggttaaatga caaatctggt aaaatatgtt ggtccaatgg ctcaaagaca   900
gttttgttat aaatttccta tattgatact ttctgctaaa ttggttcaaa acttcaaatc   960
actagccact ggatgaggta tggaacttga agagttgctt ggtggataca ttctctaatc  1020
tagggtaagt cgttagcttc aatgtcttac tgtgaattat tacatcagaa ttaagaaagt  1080
tattacacgt atgttttcac tgagtttact acactggcaa tgtggcatac atctcttact  1140
gcaaattgca gacaagtggt caatcaaatc tttttagtt gggcccaaaa tgtctgttat   1200
tggatacgtt gggccttaaa atggccccca tcagtcaaaa acatcactgc ttggagaagg  1260
atctagaaaa acttgcaagt tagttcaaac aaaataaagg aaaagaacg atctagaaga   1320
aagaaaaaaa aaggaaaaga aacccttatg gaggttccca ccactctca tatataataa    1380
catccttctc ctaaatccc                                               1399
```

<210> SEQ ID NO 9
<211> LENGTH: 1015
<212> TYPE: DNA
<213> ORGANISM: Artificial sequence
<220> FEATURE:
<223> OTHER INFORMATION: Linkage of a plant promoter and viral enhancer element

<400> SEQUENCE: 9

```
ggtccgattg agacttttca acaagggta atatccggaa acctcctcgg attccattgc    60
ccagctatct gtcactttat tgtgaagata gtggaaaagg aaggtggctc ctacaaatgc   120
catcattgcg ataaggaaa ggccatcgtt gaagatgcct ctgccgacag tggtcccaaa    180
gatggacccc cacccacgag gagcatcgtg gaaaagaag acgttccaac cacgtcttca   240
aagcaagtgg attgatgtga tggtccgatt gagacttttc aacaagggt aatatccgga    300
```

```
aacctcctcg gattccattg cccagctatc tgtcacttta ttgtgaagat agtggaaaag    360
gaaggtggct cctacaaatg ccatcattgc gataaaggaa aggccatcgt tgaagatgcc    420
tctgccgaca gtggtcccaa agatggaccc ccacccacga ggagcatcgt ggaaaaagaa    480
gacgttccaa ccacgtcttc aaagcaagtg gattgatgtg atcaagcttg atatcggaag    540
tttctctctt gagggaggtt gctcgtggaa tgggacacat atggttgtta ataaaacca     600 tttccattgt catgagattt tgaggttaat atatacttta cttgttcatt attttatttg    660
gtgtttgaat aaatgatata aatggctctt gataatctgc attcattgag atatcaaata    720
tttactctag agaagagtgt catatagatt gatggtccac aatcaatgaa attttgggga    780
gacgaacatg tataaccatt tgcttgaata accttaatta aaggtgtga ttaaatgatg     840 tttgtaacat gtagtactaa acattcataa aacacaacca acccaagagg tattgagtat    900
tcacggctaa acaggggcat aatggtaatt taaagaatga tattattta tgttaaaccc      960 taacattggt ttcggattca acgctataaa taaaaccact ctcgttgctg attcc         1015
```

<210> SEQ ID NO 10
<211> LENGTH: 840
<212> TYPE: DNA
<213> ORGANISM: Artificial sequence
<220> FEATURE:
<223> OTHER INFORMATION: Linkage of a plant promoter and viral enhancer element

<400> SEQUENCE: 10

```
catcgttgaa gatgcctctg ccgacagtgg tcccaaagat ggaccccac ccacgaggag      60 catcgtggaa aagaagacg ttccaaccac gtcttcaaag caagtggatt gatgtgatat     120
ctccactgac gtaagggatg acgcacaatc ccactatcct tcgaggcctc atcgttgaag    180
atgcctctgc cgacagtggt cccaaagatg gaccccacc cacgaggagc atcgtggaaa    240
aagaagacgt tccaaccacg tcttcaaagc aagtggattg atgtgatatc tccactgacg    300
taagggatga cgcacaatcc cactatcctt cgaagctact cgacggccgc ggaagtttct    360
ctcttgaggg aggttgctcg tggaatggga cacatatggt tgttataata accatttcc     420 attgtcatga gattttgagg ttaatatata ctttacttgt tcattatttt atttggtgtt    480
tgaataaatg atataaatgg ctcttgataa tctgcattca ttgagatatc aaatatttac    540
tctagagaag agtgtcatat agattgatgg tccacaatca atgaaatttt tgggagacga    600
acatgtataa ccatttgctt gaataacctt aattaaaagg tgtgattaaa tgatgtttgt    660
aacatgtagt actaaacatt cataaaacac aaccaaccca agaggtattg agtattcacg    720
gctaaacagg ggcataatgg taatttaaag aatgatatta ttttatgtta aaccctaagc    780
ttggtttcgg attcaacgct ataaataaaa ccactctcgt tgctgattcc atttatcgtt    840
```

<210> SEQ ID NO 11
<211> LENGTH: 705
<212> TYPE: DNA
<213> ORGANISM: Artificial sequence
<220> FEATURE:
<223> OTHER INFORMATION: Linkage of a plant promoter and viral enhancer element

<400> SEQUENCE: 11

```
ctgacgtaag ggatgacgca cctgacgtaa gggatgacgc acctgacgta agggatgacg     60
cacctgacgt aagggatgac gcactcgaga tcccatctc cactgacgta agggatgacg    120
cacaatccca ctatccttcg caagaccctt cctctatata aggaagttca tttcatttgg    180
```

```
agaggacacg ctgacaagct agcttggctg caggtaagcg gccgcggaag tttctctctt    240
gagggaggtt gctcgtggaa tgggacacat atggttgtta taataaacca tttccattgt    300
catgagattt tgaggttaat atatacttta cttgttcatt attttatttg gtgtttgaat    360
aaatgatata aatggctctt gataatctgc attcattgag atatcaaata tttactctag    420
agaagagtgt catatagatt gatggtccac aatcaatgaa attttggga gacgaacatg     480 tataaccatt tgcttgaata accttaatta aaggtgtga ttaaatgatg tttgtaacat     540
gtagtactaa acattcataa aacacaacca acccaagagg tattgagtat tcacggctaa    600
acaggggcat aatggtaatt taagaatga tattatttta tgttaaaccc taagcttggt     660
ttcggattca acgctataaa taaaaccact ctcgttgctg attcc                    705

<210> SEQ ID NO 12
<211> LENGTH: 1060
<212> TYPE: DNA
<213> ORGANISM: Arabidopsis thaliana

<400> SEQUENCE: 12
agctttcatg aatgcaacac tggaaaatga caataacata tatgaatgta gtaattacct     60
gtcctcctgt ttcagtctaa gaactttagc catatgccaa aactcagagc cttgaacacg    120
aacaactcca ccctataaac aatcataaaa cgatttacac aaagaggagc ttatcatttc    180
aaacaacaag aacatttaat attatcattt caccatgatt ttaccagaaa tttcttagag    240
attacagtga attacagtaa tttctaaact tctcagtgat tacccctcact ctcatttcga    300 ttggattctt acacagattt aaagggaaca aaaattatat gagataaaga tagagataga    360
tagggtgtgt gccttgcgag atggaagatc atcggaaaag aatcgaggaa ggccaccgcg    420
agattgattc cggagattca aatccgacgg aggagacgaa gatacagtag caaacgattt    480
gaagctagaa gtcggaagcc atgaacgaac gagactcggc aaatcggaaa acagtggccg    540
tgaagccgcc gctagcgctc tcatcattta ctcaaagctt tgaattttg gttaccattt      600 cgaagatttt ggttaatact agtttcttat cgtttcggtt tacttaaat attggtctga     660 tccggttcaa ttctaattaa attccggttc atttccacgc aattcaagga attttgctat    720
ttcaaaaata aagagaaacg gtcagaaagc gattgccaaa cagaatctaa ggaatcaaaa    780
ttcaaaatta gaaaatacgc aactcacgag gatatcaaca atcgtggtt ttaacgacaa     840 cccaattaca tcactacacg tgtatcatac gtgccgttac atacagatgg atactttcgc    900
ttataaatat agcatcaaac agctctgtaa aaacctagaa atcgaaaaaa tcagatctag    960
atctaaaaga gagcgtctt cataaacgcc cttcttcttc ttcgtcttct tccctgcaaa    1020 tctagttttct agatctttc tttcttccgc gaaacgaaac                         1060

<210> SEQ ID NO 13
<211> LENGTH: 1425
<212> TYPE: DNA
<213> ORGANISM: Nicotiana sylvestris

<400> SEQUENCE: 13
tgaattcctt taaatattcc ttttatacta aatatggcaa ctgaatatta ttttttaacg     60
aatcaaaaat taaaaaacaa atctgtaaca cctctataca taaaattgca tccaccaaat    120
gctactatct ataaactaaa cattgatggg tcttgctcat ctacccagca aaatatggta    180
ttggtggagt ttttcgaaac taccaaggca actggatcat gagatttgca ggtaaatcca    240
```

-continued

| | |
|---|---|
| atccaggcgc aaatgttcag acagaactcc ttgcactact catgggattg aaacttgttg | 300 |
| tgcaacaata tctcaacccc atcatcattg agacagatgc acatgcaatc atcggtatgt | 360 |
| ttaactcaac tactatgcac tacactaatc tcattaacga ttgcaggtta ttactcctac | 420 |
| agctggatag ccctcctata caatacatct acaaagggca aaattgtgtt gcagatagtt | 480 |
| tagccaaaca tgaagtcatg catgcacagg agagctgcat actttgtggg agaccatcat | 540 |
| cttttgcaga gccttcttac caccaagatc atatcgacac gctacaaagg aggttcgtta | 600 |
| caatcaactc cagtaactca acacaaccgc tctttgctct aactactttg tgtaatagta | 660 |
| ttgttctatc tagtactaat agtagtgttc yatctagtac taactatctt tcttgtaatg | 720 |
| attcccatac gggggtcttt gtagtaaact ctagcttagt aactatgatg cctcttatgt | 780 |
| atcttgtaaa ctgttctcat gtacctggtt aattccctat aatataagta catcttttcg | 840 |
| acaaaaaaag aagaagaaca acaacatttt agcaatgaaa aataagaaga caaacacaac | 900 |
| acatttatag aattaacatt tgaacaatga ctagtggtgc agctagttgg tgcattaccc | 960 |
| tctttgcccc ctcccccgcg cataaaaaaa tctaaaaaat aatatcagta aaagaaaga | 1020 |
| aaaaaacaaa aggaagtgtg aaagtgaaaa agactgcttt cgttttattt atactttcac | 1080 |
| acaaacaagc cacaagaatc aatcataata tattaaaatc tgcaacactc ttaaagcatg | 1140 |
| cactagtttt tataatttgt catgccagaa gttctcttaa cacaattata ccaacctttc | 1200 |
| tccaactaca gatttagctc tccatttata tttgatgcaa taacatgttt gaaacaatct | 1260 |
| catactaaga tttcatcaga caacagcaaa tctcaagtca cattctctta gcttccatat | 1320 |
| tttatccaat atgtcacaga acggcaagaa cattaatggt gcatccaagt actttttca | 1380 |
| gccgtcgacg cgccttccta ctccaggaaa agccaccatt cttgc | 1425 |

<210> SEQ ID NO 14
<211> LENGTH: 1123
<212> TYPE: DNA
<213> ORGANISM: Arabidopsis thaliana

<400> SEQUENCE: 14

| | |
|---|---|
| aagcttgtga aaacgtgaag gtttaaaac tcaaatacaa gaaatcacaa gataaataaa | 60 |
| ttcatataga ctctcagtac atacctcaga ggttttcct atagagtacc catttggata | 120 |
| gaggctcaat atgaaggaaa cttcatgatc tgcagagaaa ccaaaatgca ctcaattcaa | 180 |
| catagctaga atttagcaaa acattatgtg tcaaagtggt tcgttgagat ccaaacctgg | 240 |
| agatatatcg ggtaaagatg gcttcgaaaa cccggaaaca tcgccaatat tgctatcatc | 300 |
| agtggcctga accaaacgta ataaattttc tatataactt tccaaaataa gcgaatttag | 360 |
| ttggaacaca atacaactaa aattctaagt taaattccct ttggtttccc agatagaacg | 420 |
| attgcttttg gggaatcagg agtagccaat tcagtagaaa tcttaggtcg aaactttcta | 480 |
| ccaaccttcg atatcttaaa cgagacaccc atggattctc tccagagaga tgaagctcaa | 540 |
| acctgtctag gtactgtcaa taacgatac agaaatagaaa aagacacgag aattgaagaa | 600 |
| atcgaagaat gaattttaag aaagctagag aaattgaaac cttatgagct tgttacagag | 660 |
| aagatcatca aacaattgga tcggatagaa agcgagagaa atcaaaggtg actaagaata | 720 |
| gagcaatgaa gaattcataa acatggaatt tgtgaaacac aggtgggaaa ttttgaaga | 780 |
| agatgcgatc ggaagagaaa ggaagagaga ttattgttag ggttcttctt ctaacttcaa | 840 |
| agtagcagaa aaagaattat ctttgtgtct ctgtgcacac ttggatttcg gtttaagaca | 900 |
| aaacggaagt tgaaccagtt attaattttg gttagcttcg attaaaattt gggtaaccga | 960 |

-continued

```
gtttggggt  agaatagaca  ttttgcaaat  tagggttttg  cttgatatat  aaaatccttc    1020
acccttataa  gcctttcgtc  gcctcttcgt  gtgattact   gagtgaaaaa  agcttatcgc    1080
ggcgattagt  tcccggcgaa  gaagaagaag  agagataaga  aac                      1123
```

<210> SEQ ID NO 15
<211> LENGTH: 1727
<212> TYPE: DNA
<213> ORGANISM: Arabidopsis thaliana

<400> SEQUENCE: 15

```
cgtatgccaa  aacttgttca  tcgtgttata  tattaaacaa  caccttctgt  tctgacgata     60
aaaaatgaaa  ggcaatagta  ataatttagc  aaaaactaac  aagacatcgg  atttatttat    120
cctgtgacta  gatgtacttg  gatcatgtaa  ctggagaaat  cctacacatg  agtgtgctca    180
caggcgtttt  tatttcttgt  tctggctgtt  ctctacttca  ttcttttagc  tctagctcct    240
gttggttgct  tctgacctgt  tttccttctg  attttttctg  ttgtagactc  gagtcaacaa    300
aaggaacata  tgcagcggaa  tggaccaaat  gggagaaaca  actacgagat  actctagttg    360
caaattctga  gtatctcagt  tctattcagg  taaaaaattc  ctttgtcatt  gatggctcat    420
gaaaagcaag  aaatctgcga  ttgaatttta  aactgcttca  atgttccttc  agtacatggt    480
aaaagagtat  aagaagaagg  atgtacatat  gatgtctttg  ttttctggtt  tgcaactttc    540
aggttccatt  tgagtctatg  gttcatcaag  tgcgagaaga  gctaaaaaca  atagcgaagg    600
gtgattacaa  gccaccaagt  tcggagaaaa  gaaaacacgg  gtctattgtt  ttcgctgcca    660
tcaacttgcc  tgctactcaa  gttcacagtc  ttcttgaaaa  ggtaaccaac  caatttctta    720
tactatcata  taaaaaaaca  aaaggaatat  tgagacaaga  actcttcaac  tgccgaaaac    780
taaaggttaa  gtatgggctt  tgttattaat  taatagatgt  tattcttatc  agttggctgc    840
agcaaaccca  acaatgagat  cttttctaga  gggaaagaaa  aagagcatac  aggaaaaact    900
tgaacggtct  cacgtgacgc  tcgcccacaa  gagaagccat  ggcgtagcaa  ctgtagccag    960
ctatagtcag  cacttgaaca  gagaggtacc  cgtagagctc  accgagctca  tctacaacga   1020
caagatggct  gctctaacag  cccatgttgg  atctgtggac  ggagagaccg  tagtctccaa   1080
gaacgaatgg  ccacatgtta  cattgtggac  agcggaaggc  gttactgcga  agaggccaa    1140 cacgttacct  cagctttact  tagaaggaaa  ggcgagccgc  ttggtgatag  atcctccggt   1200
gtcaatctca  ggtcctctgg  agttttctg   aatacttgat  taaacatgga  agtttctctc   1260
ttgagggagg  ttgctcgtgg  aatgggacac  atatggttgt  tataataaac  catttccatt   1320
gtcatgagat  tttgaggtta  atatatactt  tacttgttca  ttattttatt  tggtgtttga   1380
ataaatgata  taaatggctc  ttgataatct  gcattcattg  agatatcaaa  tatttactct   1440
agagaagagt  gtcatataga  ttgatggtcc  acaatcaatg  aaattttggg  agacgaaca    1500 tgtataacca  tttgcttgaa  taaccttaat  taaaaggtgt  gattaaatga  tgtttgtaac   1560
atgtagtact  aaacattcat  aaaacacaac  caacccaaga  ggtattgagt  attcacggct   1620 aaacagggc   ataatggtaa  tttaaagaat  gatattattt  tatgttaaac  cctaacattg   1680
gtttcggatt  caacgctata  aataaaacca  ctctcgttgc  tgattcc                  1727
```

<210> SEQ ID NO 16
<211> LENGTH: 1054
<212> TYPE: DNA
<213> ORGANISM: Nicotiana tabacum

<400> SEQUENCE: 16

```
atcatgtata tttgtgcata tccatgaaaa tttgtgttat atatacgata tataatgtga      60
tacacatagg cgtccataaa agaattgtgt tgtatacacg atatacaaag tgatatacag     120
atgtccttaa aaatatgtgt gtgatataca ttgatgtaca caatatgcaa cgcgatatac     180
acatgtcaca gttggatttt aggtctgatg ttttacatga aatcagtcta aatcacttct     240
aatcttgctc aaattttgta tatagccccg tttaggtatt ttcaaccaat ttcactcaca     300
ccactcgttc aatctaacca aaaaaaagaa gagagaagaa aaacaaagtt gaaatgaatt     360
tttctctctt agttttttgct tataattttt ctgattacct tttcaccccca ctgatttttt    420
ttgcataatt tgcaaggatt tttgctaaac tatgagagcg aaagaaaaga gatagaagaa     480
gaaatacaag gagagaaagg gggagggacg cagtgaacaa aaaaagaagt tagcggcgaa     540
gagggggggg ggggggaagc agacggtttg gggccaattg tttgagagag aatatataag     600
agagtagttt ttttaggatt tggctatata atgtcaattt tttgggggcta tcttttccta    660
acctaatata agactaaaaa attgtcaatt cctgttatgt gttatcacct ggtgccattt     720
tctcatagtt atacatatag tgaaaggaaa agagggtatt agtgccaatt ttgtaaagag     780
gttagaccta aattaggccc aagaggccca atagaaaatc tagccctcaa ttttgtggaa     840
tccacgtcac cgacttcttg cattaccacc cgaagcggct ccgtattgat cctgtaactc     900
ccaatttcgg gtcaaaatag gaatttcaaa tacagaagcc aaaaaaaaaa ggaaagtaat     960
ccaaaacagt attcagaaag accataaaaa aacactagtc tcaatctttc tcttttcctc    1020
tttcctgaac tcctgcggcg tagatccgag gagt                                1054
```

<210> SEQ ID NO 17
<211> LENGTH: 925
<212> TYPE: DNA
<213> ORGANISM: Arabidopsis thaliana

<400> SEQUENCE: 17

```
ttacttgcga cagaaacagc tttgatatat tattactcac ccgttatcga tatggaatat      60
atactttaag aactcactaa atcatatcct tcatgtcggt ttaaagatta gtcacgtatc     120
tgcacattct gtaagtatag taatctcata aaaaacctgg tctctgttct ctgtgaatcc     180
ataggttatt gcactggcgt actactgtat atcatatttc cctggtggat catcgggaat     240
gaagttcctc agttctactc ttacctcctc tgtcttccga atgtttggga gatgagcttt     300
cgctttgacc tatgcaaaga aaataacttg attctctcgt gtataaagaa agatgaaaga     360
tcttcaacag tggttaaatg acaaatctgg taaaatatgt tggtccaatg gctcaaagac     420
agttttgtta taaatttcct atattgatac tttctgctaa attggttcaa aacttcaaat     480
cactagccac tggatgaggt atggaacttg aagagttgct tggtggatac attctctaat     540
ctagggtaag tcgttagctt caatgtctta ctgtgaatta ttcatcaga attaagaaag     600
ttattacacg tatgttttca ctgagtttac tacactggca atgtggcata catctcttac     660
tgcaaattgc agacaagtgg tcaatcaaat cttttttagt tgggcccaaa atgtctgtta    720
ttggatacgt tgggccttaa aatggccccc atcagtcaaa acatcactg cttggagaag     780
gatctagaaa aacttgcaag ttagttcaaa caaaataaag gaaaagaac gatctagaag     840
aaagaaaaaa aaaggaaaag aaacccttat ggaggttccc acaccactct atatataata     900
acatccttct cctaaatccc gcatc                                           925
```

<210> SEQ ID NO 18
<211> LENGTH: 2316
<212> TYPE: DNA
<213> ORGANISM: Arabidopsis thaliana

<400> SEQUENCE: 18

```
gaattctgat gtctcaaatc aagcatattt ttctggaact tctgggaaag gaaatggtga      60
tcttcgtgtt gaaaacccct tagttggttt agttcctaga acactggtt  cgctttcgag     120 ttctttagca gcggaaaggc aaagatacgt ggagcatttt ggctatagct caaaaaaagg     180
tcataagtta tctgtagaat ctgatcttca agttgaggtt tctgaaattg gatcacctcc     240
cactacagtt gatgggaata attcttctga tgaagaaaaa tcacgtattg tcaacgaatc     300
agacattggg aaggagacgg gatttagtgg tgaggagagc attgtggata aactgaaga     360 aactcaaatg ttaccagtgg agaaagttga taaagattta aatgaaacga tttctaaggt     420
ctctccagaa acttatgtag ccaaacaagt tgagggtctg tctgatggta ctgatatcaa     480
cggaagatct gaggaagaag agagctcaaa atccggacgc tttccactgg aaaattcaga     540
caaaggattc tatatacatg aagagtcaac agttcctcac atcaatgaag ttatttcgag     600
aagagaagag gttatatagt tcttgttctt gtcaggtttt atggaaatat gattgctact     660
tgcaatgtgt ttctcaaaat gttgaatttg aatatattcc ttgtaccgtt atgacaggaa     720
cgtgtccaaa acttgactga tgagatgaag ataaatgatg actctgatga acctgaagcc     780
tttgaaagaa gaacaaatca agaaccccaa gaacattttg ggggaaatga tggagaccaa     840
tcaactcaag agttgcaaga acttgtggaa cctgaagttt caatgtgaa caatgtcaca     900 tcagacgagt ctgctacttc cccaagatca gtgttaccag acatgttgtt atctttagac     960
cagacttata ctctgacttc tgagagtttg gaacatacat tagatagtca acctccgcca    1020
gtgattccat atccggaatc tccacagaat caatcaggtg ttgatgggaa cagtagatga    1080
agtgtgctca gagatcagtt tcaatgcaag tacttgaact gaaatgtacc tttaacaaaa    1140
tgatgacgtg tgttttctaa aacaaggata gtctgaggca agtgagaagc tagagaagaa    1200
gtttcttctt tagatgccat tgtccttttg ttgaacactc aacaaattca ggcttatgca    1260
gtgtagagga tttaggttcc ctagctaaat tttatgtata tgctaaagtt gaacattaat    1320
gtgtggaatt tgatttagtg aagtgatcat cattttgttt gatgataact gagatataat    1380
ttatgttgtc ttttaaaaag tttaatgtat tatagtatgg gaaatctgat aatgattggt    1440
tatttctaaa ttttagtaaa ttactttctc ttttagttta aaataaataa aggatcgttg    1500
attatcaaca agataaaatt ttttacaaca acaacaactc ttctcctgat tatgaagctc    1560
taaatatttt ttaatattaa tgaccaatta attttaccct ttaatataag tggtcaccct   1620
ttttttttaa aaccgtatat caacttatct gcgttttctc cgtattctct catgggatta    1680
atatttgctt ttaaatgtgg ataaatgatg tccaaaaaaa catttggata aaattttatc    1740
catgctgaaa aatgtataac aagaattttt ttttttttt  taataacaaa tacttataat    1800
tcttacgatt atataggtgt agattattat tcttttcat  gcaatgacca tgcggataat    1860
tttgtctaaa ttttatccaa aacttttttc acactcattt cttataggaa aaatattcta    1920
cccagacttg cttgtgtaat tatatgaatg ttaaaaatat tacataatca aaagccaagc    1980
tctgagatca tatatgtcgt ataaaaaatt attattgtgt cgatcaaacg tcattatctt    2040
ttacttaaaa aaaaaagagt ttttatttct taatctcgat attgatctaa acgatttaat    2100
tgtttattta tttaaatgat aatatcttaa tatcaaaaca catatatctt atcagtaatt    2160
```

```
atccacattt attctcagat aaaacaggat cgagtcagaa gaaaaattcg ttcaaaaaga    2220
ttcagttgtt aaatcttagt ttatccaaaa ccctcacact catctataaa agaaacccca    2280
tctcctctct taggcatttg agttttattt acgatc                              2316

<210> SEQ ID NO 19
<211> LENGTH: 537
<212> TYPE: DNA
<213> ORGANISM: Figwort mosaic virus

<400> SEQUENCE: 19
aattctcagt ccaaagcctc aacaaggtca gggtacagag tctccaaacc attagccaaa      60
agctacagga gatcaatgaa gaatcttcaa tcaaagtaaa ctactgttcc agcacatgca     120
tcatggtcag taagtttcag aaaaagacat ccaccgaaga cttaaagtta gtgggcatct     180
ttgaaagtaa tcttgtcaac atcgagcagc tggcttgtgg ggaccagaca aaaaaggaat     240
ggtgcagaat tgttaggcgc acctaccaaa agcatctttg cctttattgc aaagataaag     300
cagattcctc tagtacaagt ggggaacaaa ataacgtgga aaagagctgt cctgacagcc     360
cactcactaa tgcgtatgac gaacgcagtg acgaccacaa agaattagc ttgagctcag      420 gatttagcag cattccagat tgggttcaat caacaaggta cgagccatat cactttattc     480
aaattggtat cgccaaaacc aagaaggaac tcccatcctc aaaggtttgt aaggaag        537

<210> SEQ ID NO 20
<211> LENGTH: 522
<212> TYPE: DNA
<213> ORGANISM: Cauliflower mosaic virus

<400> SEQUENCE: 20
ggtccgattg agactttca acaaagggta atatccggaa acctcctcgg attccattgc       60
ccagctatct gtcactttat tgtgaagata gtggaaaagg aaggtggctc ctacaaatgc     120
catcattgcg ataaaggaaa ggccatcgtt gaagatgcct ctgccgacag tggtcccaaa     180
gatggacccc cacccacgag gagcatcgtg gaaaagaag acgttccaac cacgtcttca      240
aagcaagtgg attgatgtga tggtccgatt gagacttttc aacaaagggt aatatccgga     300
aacctcctcg gattccattg cccagctatc tgtcacttta ttgtgaagat agtggaaaag     360
gaaggtggct cctacaaatg ccatcattgc gataaaggaa aggccatcgt tgaagatgcc     420
tctgccgaca gtggtcccaa agatggaccc ccacccacga ggagcatcgt ggaaaagaa      480 gacgttccaa ccacgtcttc aaagcaagtg gattgatgtg at                        522

<210> SEQ ID NO 21
<211> LENGTH: 333
<212> TYPE: DNA
<213> ORGANISM: Cauliflower mosaic virus

<400> SEQUENCE: 21
catcgttgaa gatgcctctg ccgacagtgg tcccaaagat ggaccccac ccacgaggag        60 catcgtggaa aagaagacg ttccaaccac gtcttcaaag caagtggatt gatgtgatat      120
ctccactgac gtaagggatg acgcacaatc ccactatcct tcgaggcctc atcgttgaag     180
atgcctctgc cgacagtggt cccaaagatg accccacc cacgaggagc atcgtggaaa        240 agaagacgt tccaaccacg tcttcaaagc aagtggattg atgtgatatc tccactgacg      300
taagggatga cgcacaatcc cactatcctt cga                                  333
```

-continued

```
<210> SEQ ID NO 22
<211> LENGTH: 185
<212> TYPE: DNA
<213> ORGANISM: Artificial sequence
<220> FEATURE:
<223> OTHER INFORMATION: tandem multimer of CaMV as1 enhancer

<400> SEQUENCE: 22
ctgacgtaag ggatgacgca cctgacgtaa gggatgacgc acctgacgta agggatgacg        60
cacctgacgt aagggatgac gcactcgaga tccccatctc cactgacgta agggatgacg       120
cacaatccca ctatccttcg caagaccctt cctctatata aggaagttca tttcatttgg       180
agagg                                                                   185
```

US 8,940,962 B2

CHIMERIC PROMOTER COMPRISING FMV ENHANCER AND HSP81-2 PROMOTER AND PLANTS TRANSFORMED THEREWITH

REFERENCE TO RELATED APPLICATIONS

This application claims priority to U.S. Provisional Application No. 61/098,950, filed on Sep. 22, 2008, which is incorporated herein by reference in its entirety.

INCORPORATION OF SEQUENCE LISTING

The Sequence Listing, which is a part of the present disclosure, includes a computer readable 42 KB file entitled "MONS225US_ST25.txt" comprising nucleotide and/or amino acid sequences of the present invention submitted via EFS-Web. The subject matter of the Sequence Listing is incorporated herein by reference in its entirety.

FIELD OF THE INVENTION

The invention relates to the field of plant molecular biology and plant genetic engineering and DNA molecules useful for modulating gene expression in plants.

BACKGROUND

Promoters are genetic elements that regulate gene activity by modulating the transcription of an operably linked transcribable DNA molecule. Promoters may be defined as constitutive, i.e., generally always active, or by their temporal, spatial, developmental, tissue, environmental, physiological, pathological, cell cycle, and/or chemically responsive expression pattern, and any combination thereof, as well as by quantitative or qualitative indications. Optimal expression of a transgene in a plant can be achieved by using novel chimeric promoters.

SUMMARY OF THE INVENTION

The present invention provides novel chimeric promoters for use in plants. The present invention also provides DNA constructs comprising the chimeric promoters. The present invention also provides transgenic plant cells, plants, and seeds comprising the chimeric promoters operably linked to a transcribable DNA molecule. The present invention also provides methods of making and using the chimeric promoters, the DNA constructs comprising the chimeric promoters, and the transgenic plant cells, plants, and seeds comprising the chimeric promoters operably linked to a transcribable DNA molecule

BRIEF DESCRIPTION OF THE SEQUENCE LISTING

Figure 1:
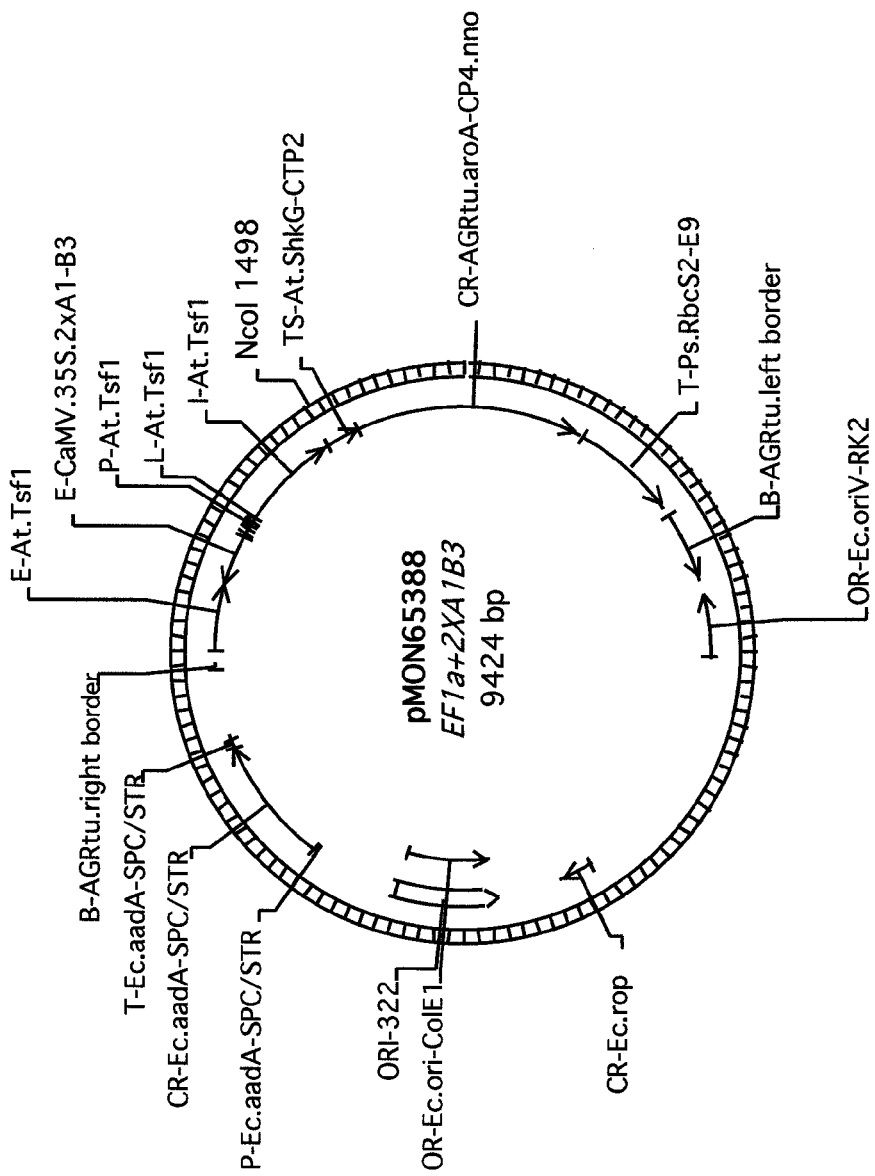
FIG. 1 illustrates the pMON65388 DNA construct, comprising a right border region from *Agrobacterium tumefaciens* (B-AGRtu.right border), a chimeric promoter comprising an enhancer segment (E-At.Tsf1) from *Arabidopsis thaliana* elongation factor 1-alpha promoter linked to a duplicated A1-B3 enhancer segment from Cauliflower mosaic virus 35S promoter (E-CaMV.35S.2xA1-B3) linked to segment of the *Arabidopsis thaliana* elongation factor 1-alpha promoter (P-At.Tsf1), linked to a leader segment from At.Tsf1 (L-At.Tsf1), linked to a intron segment from At.Tsf1 (I-At.Tsf1), linked to a transit signal peptide coding sequence from *Arabidopsis thaliana* ShkG (TS-At.ShkG-CTP2), linked to the artificial coding sequence for the glyphosate resistant EPSPS from *Agrobacterium tumefaciens* CP4 (CR-AGRtu.aroA-CP4.nno), linked to a 3' termination region from pea rubisco small subunit (T-Ps.Rbc.S2-E9), linked to a left border region from *Agrobacterium tumefaciens* (B-AGRtu.left border).

SEQ ID NO: 1 is the sequence of the chimeric promoter AtTSF1/2XA1B3/I-AtTSF1 (illustrated in pMON65388 in FIG. 1).

Figure 2:
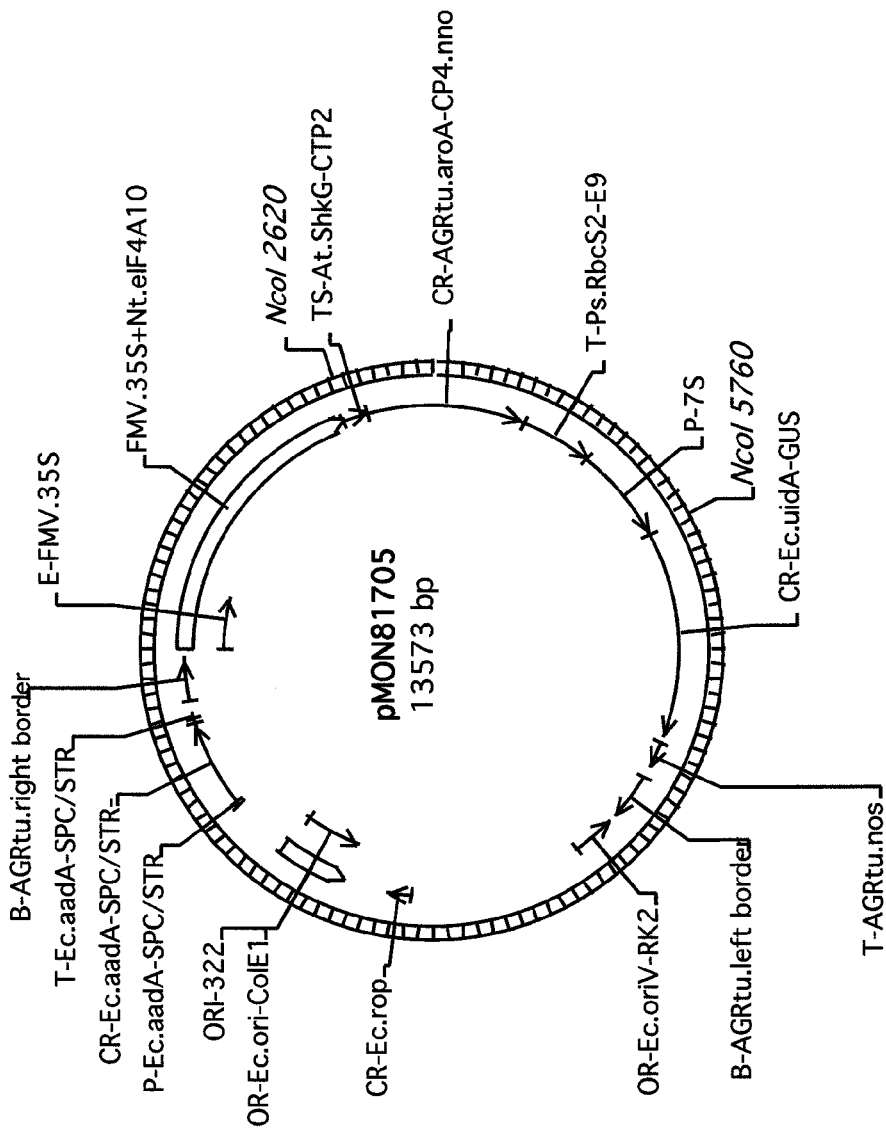
FIG. 2 illustrates the pMON81705 DNA construct, comprising a right border region from *Agrobacterium tumefaciens* (B-AGRtu.right border), a chimeric promoter comprising an enhancer segment (E-FMV.35S) from Figwort mosaic virus promoter linked to a promoter segment from *Nicotiana tabacum* initiation factor 4A10 (P-Nt.eIF4A10) linked to a leader segment from *Nicotiana tabacum* initiation factor 4A10 (L-Nt.eIF4A10) linked to an intron segment from *Nicotiana tabacum* initiation factor 4A10 (I-Nt.elf4A10) linked to a transit signal peptide coding sequence from *Arabidopsis thaliana* ShkG (TS-At.ShkG-CTP2), linked to the artificial coding sequence for the glyphosate resistant EPSPS from *Agrobacterium tumefaciens* CP4 (CR-AGRtu.aroA-CP4.nno), linked to a 3' termination region from pea rubisco small subunit (T-Ps.Rbc.S2-E9), linked to a left border region from *Agrobacterium tumefaciens* (B-AGRtu.left border).

SEQ ID NO: 2 is the sequence of the chimeric promoter FMV/NteIF4A10 (illustrated in pMON81705 in FIG. 2).

Figure 3:
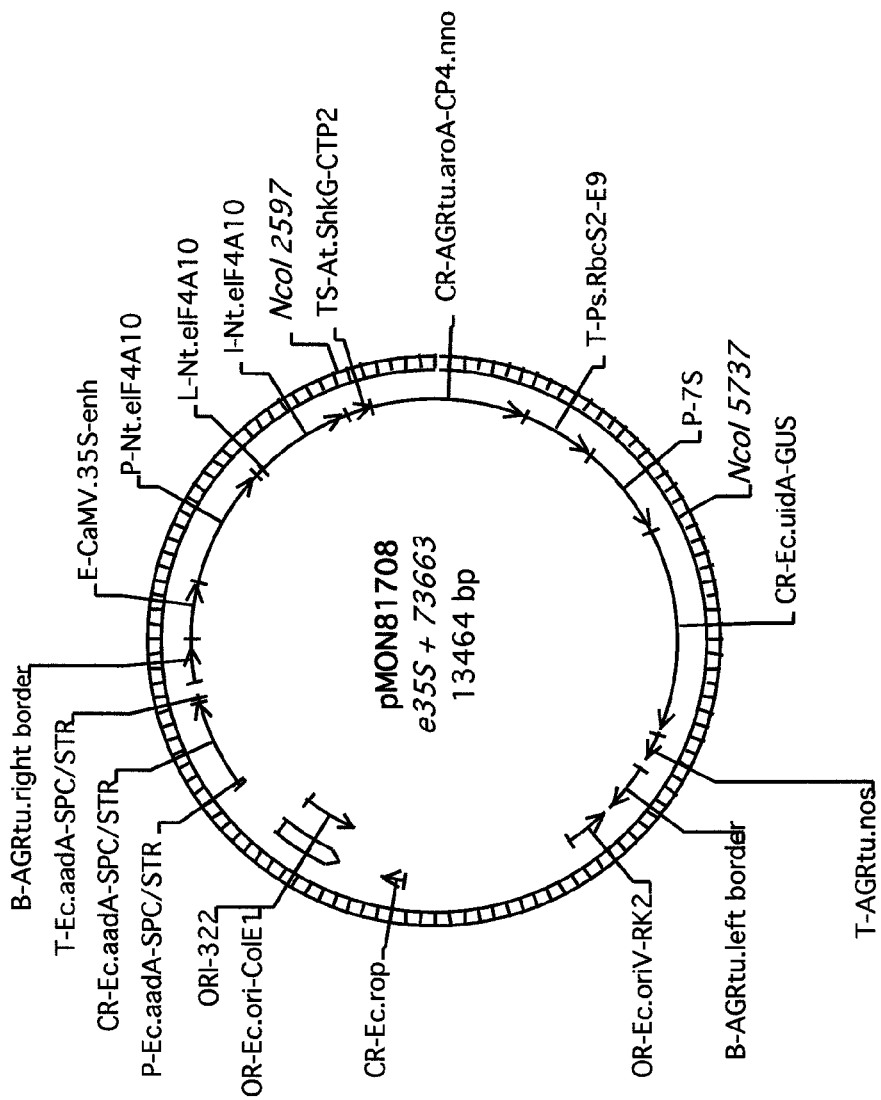
FIG. 3 illustrates the pMON81708 DNA construct, comprising a right border region from *Agrobacterium tumefaciens* (B-AGRtu.right border), a chimeric promoter comprising an enhancer segment (E-CaMV.35S-enh) from Cauliflower mosaic virus 35S promoter linked to a promoter segment from *Nicotiana tabacum* initiation factor 4A10 gene (P-Nt.eIF4A10) linked to a leader segment from *Nicotiana tabacum* initiation factor 4A10 gene (L-Nt.eIF4A10) linked to an intron segment from *Nicotiana tabacum* initiation factor 4A10 gene (1-Nt.elf4A10) linked to a transit signal peptide coding sequence from *Arabidopsis thaliana* ShkG (TS-At.ShkG-CTP2), linked to the artificial coding sequence for the glyphosate resistant EPSPS from *Agrobacterium tumefaciens* CP4 (CR-AGRtu.aroA-CP4.nno), linked to a 3' termination region from pea rubisco small subunit (T-Ps.Rbc.S2-E9), linked to a left border region from *Agrobacterium tumefaciens* (B-AGRtu.left border).

SEQ ID NO: 3 is the sequence of the chimeric promoter e35S/NteIF4A10 (illustrated in pMON81708 in FIG. 3).

Figure 4:
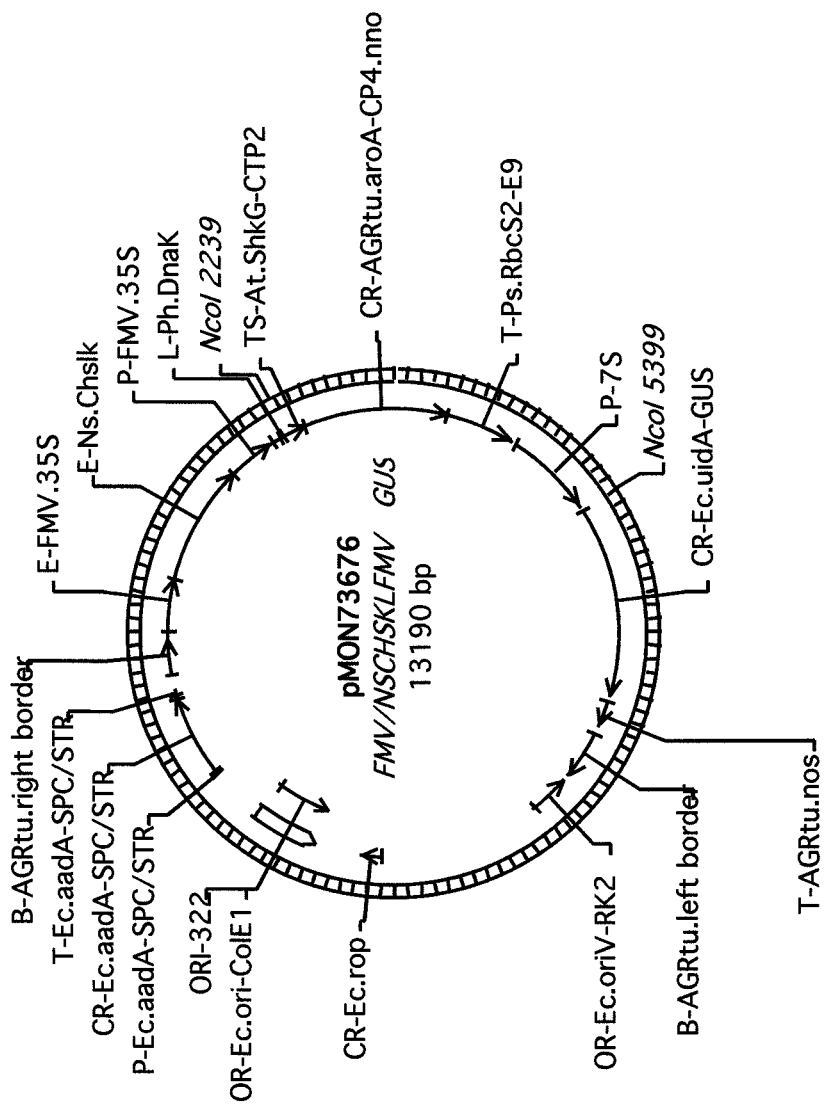
FIG. 4 illustrates the pMON73676 DNA construct, a right border region from *Agrobacterium tumefaciens* (B-AGRtu.right border), a chimeric promoter comprising an enhancer segment (E-FMV.35S) from Figwort mosaic virus promoter linked to a enhancer segment from *Nicotiana sylvestris* chalcone synthase gene promoter (E-Ns.Chslk) linked to a promoter segment (P-FMV.35S) from Figwort mosaic virus 35S promoter linked to a leader segment from *Petunia hybrida* DnaK (L-Ph.DnaK) linked to a transit signal peptide coding sequence from *Arabidopsis thaliana* ShkG (TS-At.ShkG-CTP2), linked to the artificial coding sequence for the glyphosate resistant EPSPS from *Agrobacterium tumefaciens* CP4 (CR-AGRtu.aroA-CP4.nno), linked to a 3' termination region from pea rubisco small subunit (T-Ps.Rbc.S2-E9), linked to a left border region from *Agrobacterium tumefaciens* (B-AGRtu.left border).

SEQ ID NO: 4 is the sequence of the chimeric promoter FMV/NsChslk/FMV (illustrated in pMON73676 in FIG. 4).

Figure 5:
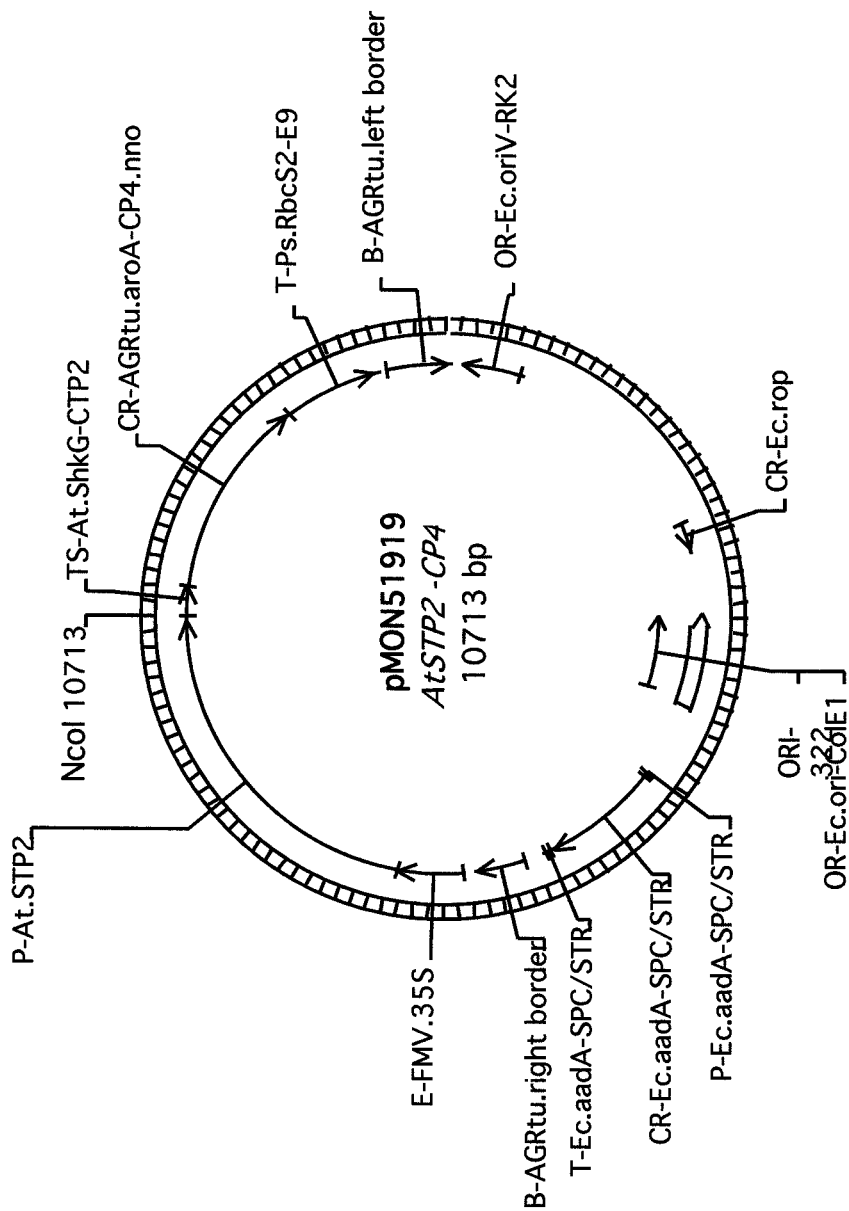
FIG. 5 illustrates the pMON51919 DNA construct, a right border region from *Agrobacterium tumefaciens* (B-AGRtu.right border), a chimeric promoter comprising an enhancer segment (E-FMV.35S) from Figwort mosaic virus promoter linked to a promoter segment from *Arabidopsis thaliana* STP (P-At.STP2) linked to a transit signal peptide coding sequence from *Arabidopsis thaliana* ShkG (TS-At.ShkG-CTP2), linked to the artificial coding sequence for the glyphosate resistant EPSPS from *Agrobacterium tumefaciens* CP4 (CR-AGRtu.aroA-CP4.nno), linked to a 3' termination region from pea rubisco small subunit (T-Ps.Rbc.S2-E9), linked to a left border region from *Agrobacterium tumefaciens* (B-AGRtu.left border).

SEQ ID NO: 5 is the sequence of the chimeric promoter FMV/STP (illustrated as pMON51919 in FIG. 5).

Figure 6:
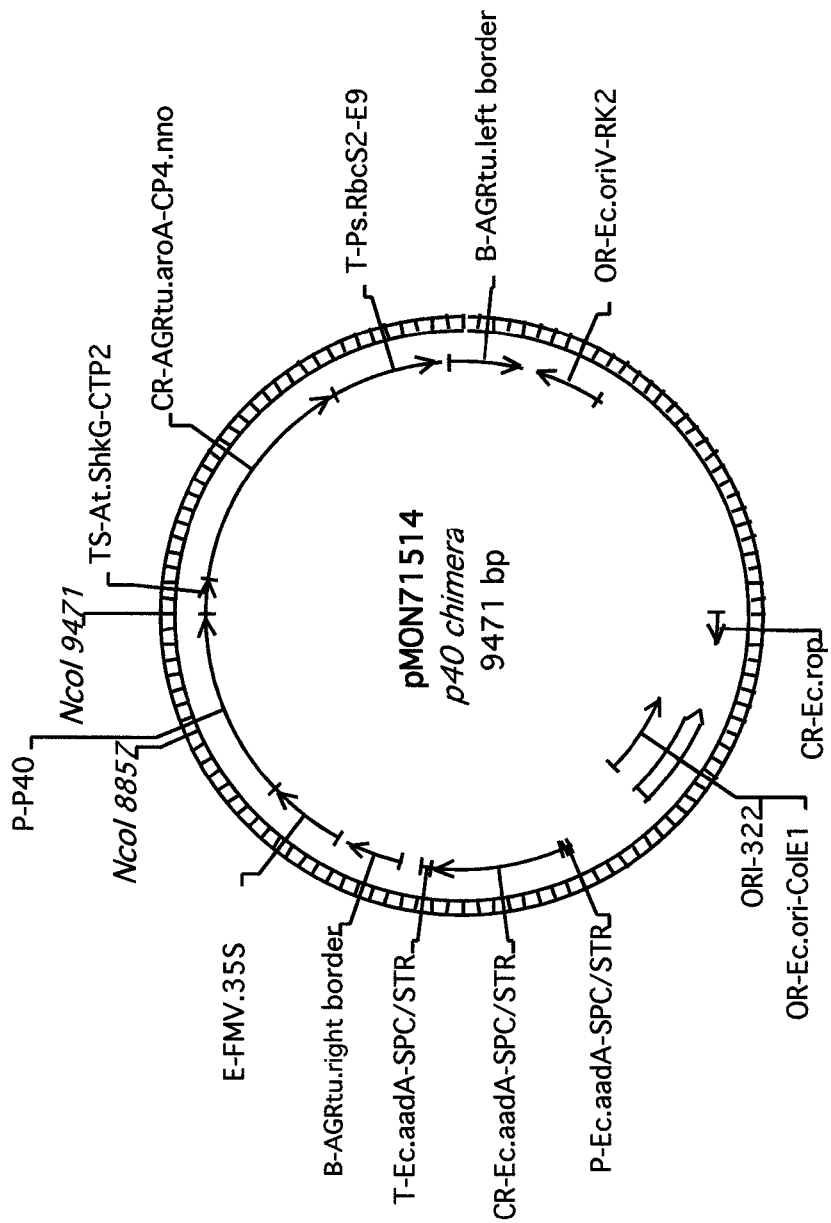
FIG. 6 illustrates the pMON71514 DNA construct, a right border region from *Agrobacterium tumefaciens* (B-AGRtu.right border), a chimeric promoter comprising an enhancer segment (E-FMV.35S) from Figwort mosaic virus promoter linked to a promoter segment from *Arabidopsis thaliana* P40 gene (P-P40) linked to a transit signal peptide coding sequence from *Arabidopsis thaliana* ShkG (TS-At.ShkG-CTP2), linked to the artificial coding sequence for the glyphosate resistant EPSPS from *Agrobacterium tumefaciens* CP4 (CR-AGRtu.aroA-CP4.nno), linked to a 3' termination region from pea rubisco small subunit (T-Ps.Rbc.S2-E9), linked to a left border region from *Agrobacterium tumefaciens* (B-AGRtu.left border).

SEQ ID NO: 6 is the sequence of the chimeric promoter FMV/P40 (illustrated as pMON71514 in FIG. 6).

Figure 7:
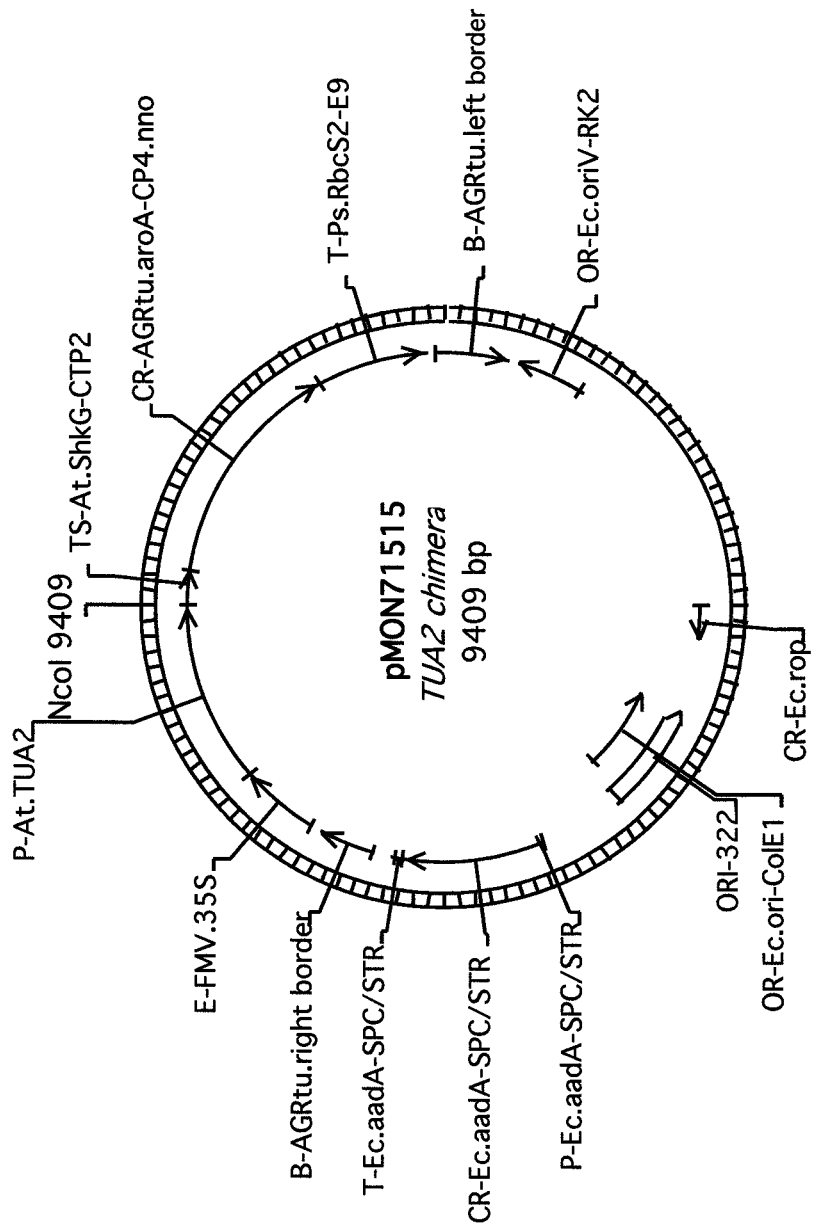
FIG. 7 illustrates the pMON71515 DNA construct, comprising a right border region from *Agrobacterium tumefaciens* (B-AGRtu.right border), a chimeric promoter comprising an enhancer segment (E-FMV.35S) from Figwort mosaic virus promoter linked to a promoter segment from *Arabidopsis thaliana* tubulin (P-At.TUA2) linked to a transit signal peptide coding sequence from *Arabidopsis thaliana* ShkG (TS-At.ShkG-CTP2), linked to the artificial coding sequence for the glyphosate resistant EPSPS from *Agrobacterium tumefaciens* CP4 (CR-AGRtu.aroA-CP4.nno), linked to a 3' termination region from pea rubisco small subunit (T-Ps.Rbc.S2-E9), linked to a left border region from *Agrobacterium tumefaciens* (B-AGRtu.left border).

SEQ ID NO: 7 is the sequence of the chimeric promoter FMV/TAU2 (illustrated as pMON71515 in FIG. 7).

Figure 8:
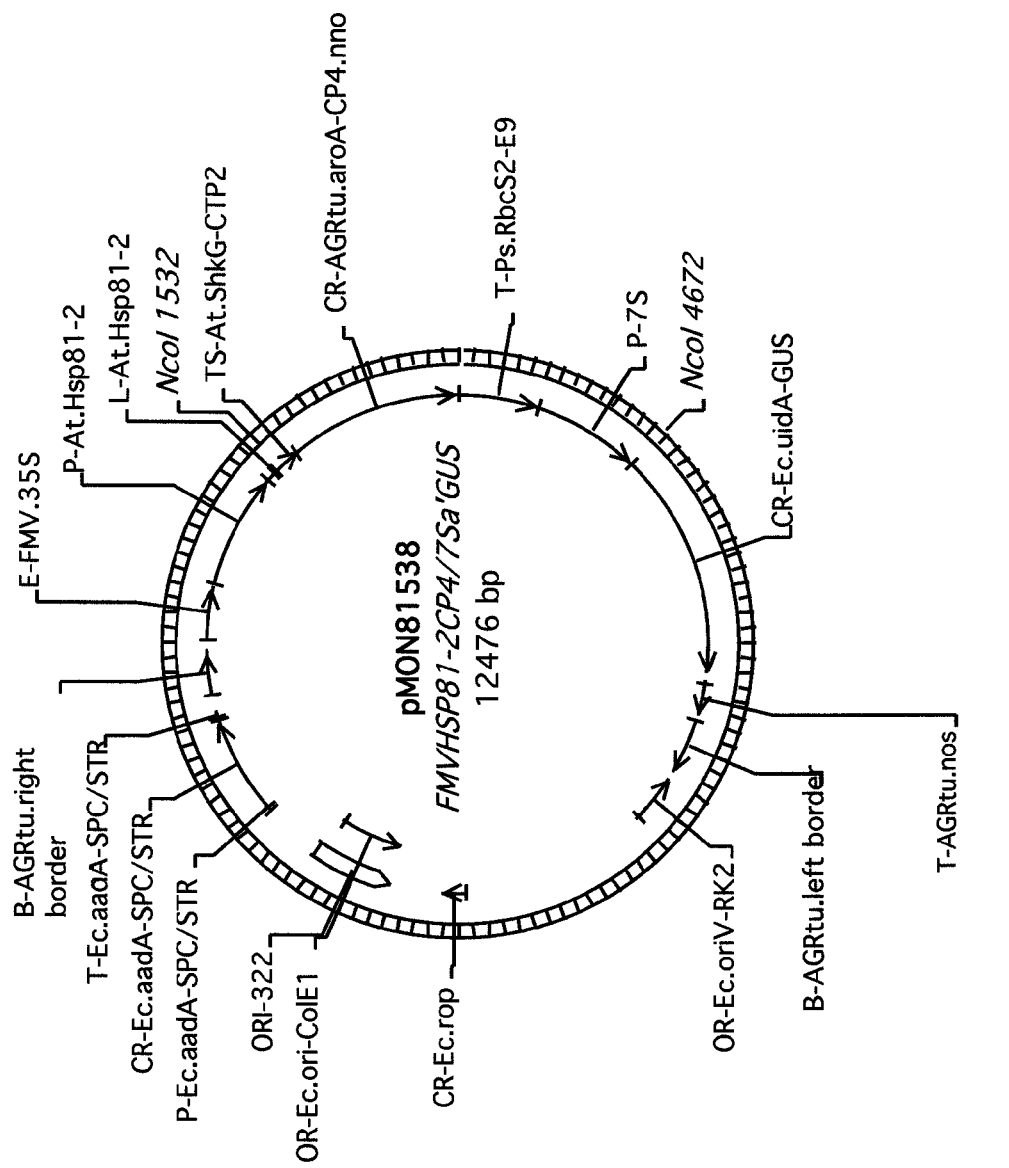
FIG. 8 illustrates the pMON81538 DNA construct, comprising a right border region from *Agrobacterium tumefaciens* (B-AGRtu.right border), a chimeric promoter comprising an enhancer segment (E-FMV.35S) from Figwort mosaic virus promoter linked to a promoter segment from *Arabidopsis thaliana* heat shock protein 81 gene (P-At.Hsp81) linked to a leader segment from *Arabidopsis thaliana* heat shock protein 81 gene (P-At.Hsp81) linked to a transit signal peptide coding sequence from *Arabidopsis thaliana* ShkG (TS-At.ShkG-CTP2), linked to the artificial coding sequence for the glyphosate resistant EPSPS from *Agrobacterium tumefaciens* CP4 (CR-AGRtu.aroA-CP4.nno), linked to a 3' termination region from pea rubisco small subunit (T-Ps.Rbc.S2-E9), linked to a left border region from *Agrobacterium tumefaciens* (B-AGRtu.left border).

SEQ ID NO: 8 is the sequence of the chimeric promoter FMV/Hsp81-2 (illustrated as pMON81538 in FIG. 8).

Figure 9:
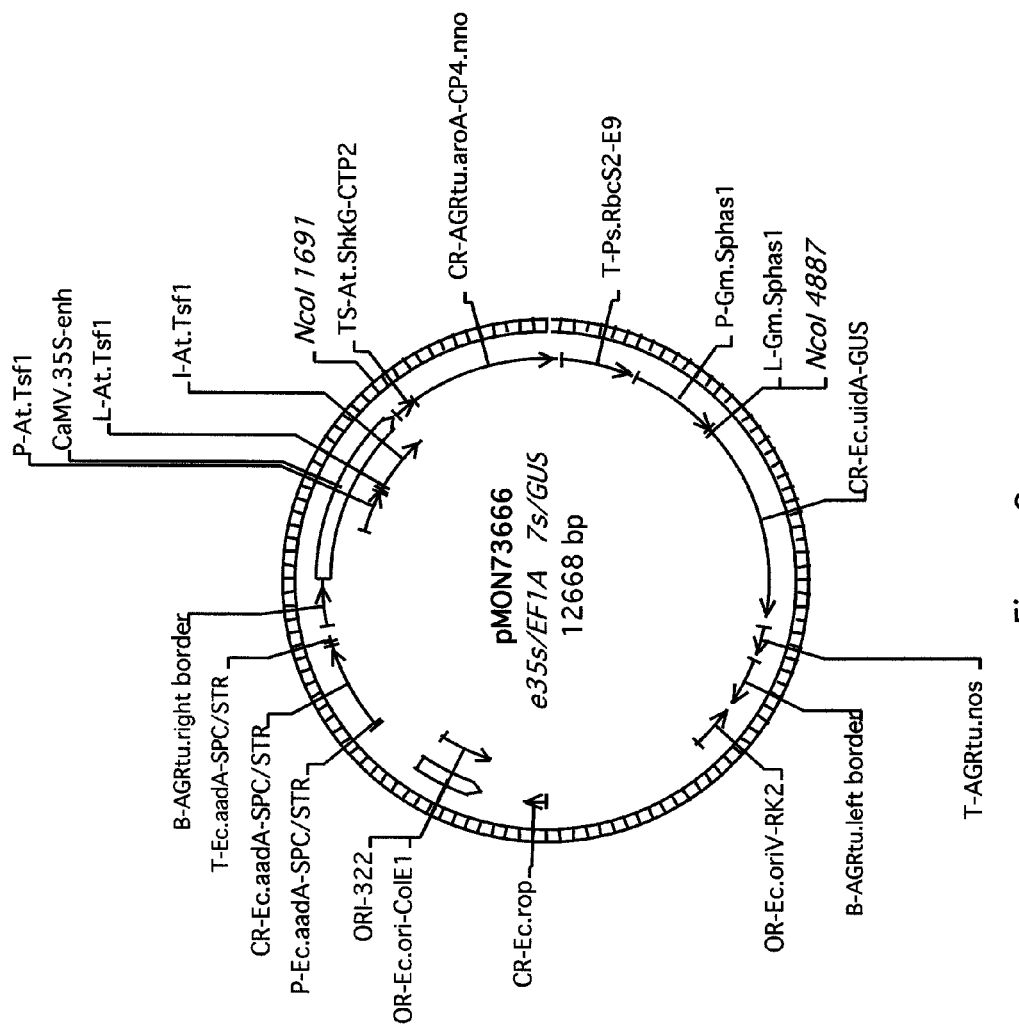
FIG. 9 illustrates the pMON73666 DNA construct, comprising a right border region from *Agrobacterium tumefaciens* (B-AGRtu.right border), a chimeric promoter comprising an enhancer segment (E-CaMV.35S-enh) from Cauliflower mosaic virus 35S promoter linked to a promoter segment from *Arabidopsis thaliana* elongation factor 1 alpha gene (P-At.Tsf1) linked to a leader segment from *Arabidopsis thaliana* elongation factor 1 alpha gene (L-At.Tsf1) linked to an intron segment from *Arabidopsis thaliana* elongation factor 1 alpha gene (I-At.Tsf1) linked to a transit signal peptide coding sequence from *Arabidopsis thaliana* ShkG (TS-At.ShkG-CTP2), linked to the artificial coding sequence for the glyphosate resistant EPSPS from *Agrobacterium tumefaciens* CP4 (CR-AGRtu.aroA-CP4.nno), linked to a 3' termination region from pea rubisco small subunit (T-Ps.Rbc.S2-E9), linked to a left border region from *Agrobacterium tumefaciens* (B-AGRtu.left border).

SEQ ID NO: 9 is the sequence of the chimeric promoter e35S/AtTSF1 (illustrated as pMON73666 in FIG. 9).

Figure 10:
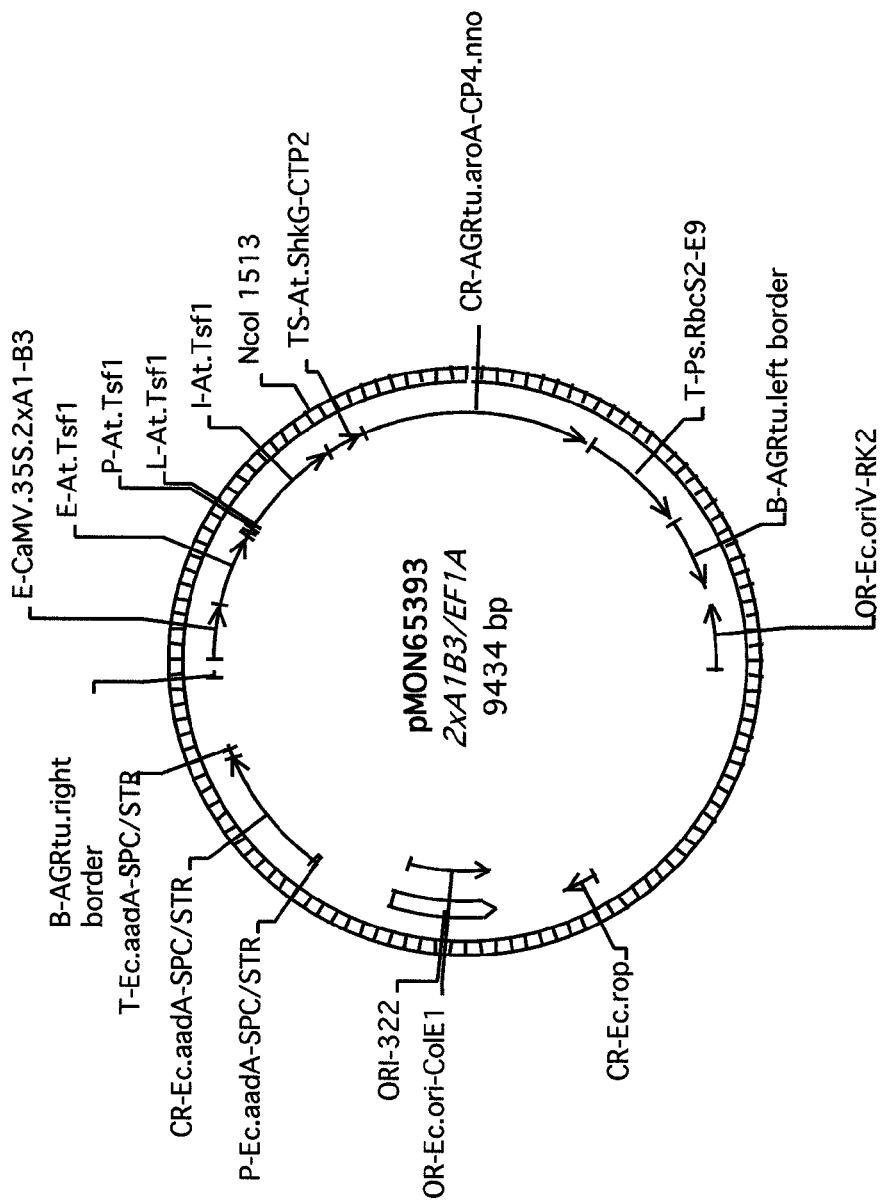
FIG. 10 illustrates the pMON65393 DNA construct, comprising a right border region from *Agrobacterium tumefaciens* (B-AGRtu.right border), a chimeric promoter comprising an enhancer segment (E-CaMV.35S-enh) from Cauliflower mosaic virus 35S promoter linked to a promoter enhancer segment from *Arabidopsis thaliana* elongation factor 1 alpha gene (E-At.Tsf1) linked to a promoter segment from *Arabidopsis thaliana* elongation factor 1 alpha gene (P-At.Tsf1) linked to a leader segment from *Arabidopsis thaliana* elongation factor 1 alpha gene (L-At.Tsf1) linked to an intron segment from *Arabidopsis thaliana* elongation factor 1 alpha gene (I-At.Tsf1) linked to a transit signal peptide coding sequence from *Arabidopsis thaliana* ShkG (TS-At.ShkG-CTP2), linked to the artificial coding sequence for the glyphosate resistant EPSPS from *Agrobacterium tumefaciens* CP4 (CR-AGRtu.aroA-CP4.nno), linked to a 3' termination region from pea rubisco small subunit (T-Ps.Rbc.S2-E9), linked to a left border region from *Agrobacterium tumefaciens* (B-AGRtu.left border).

SEQ ID NO: 10 is the sequence of the chimeric promoter 2XA1B3/AtTSF1 (illustrated as pMON65393 in FIG. 10)

Figure 11:
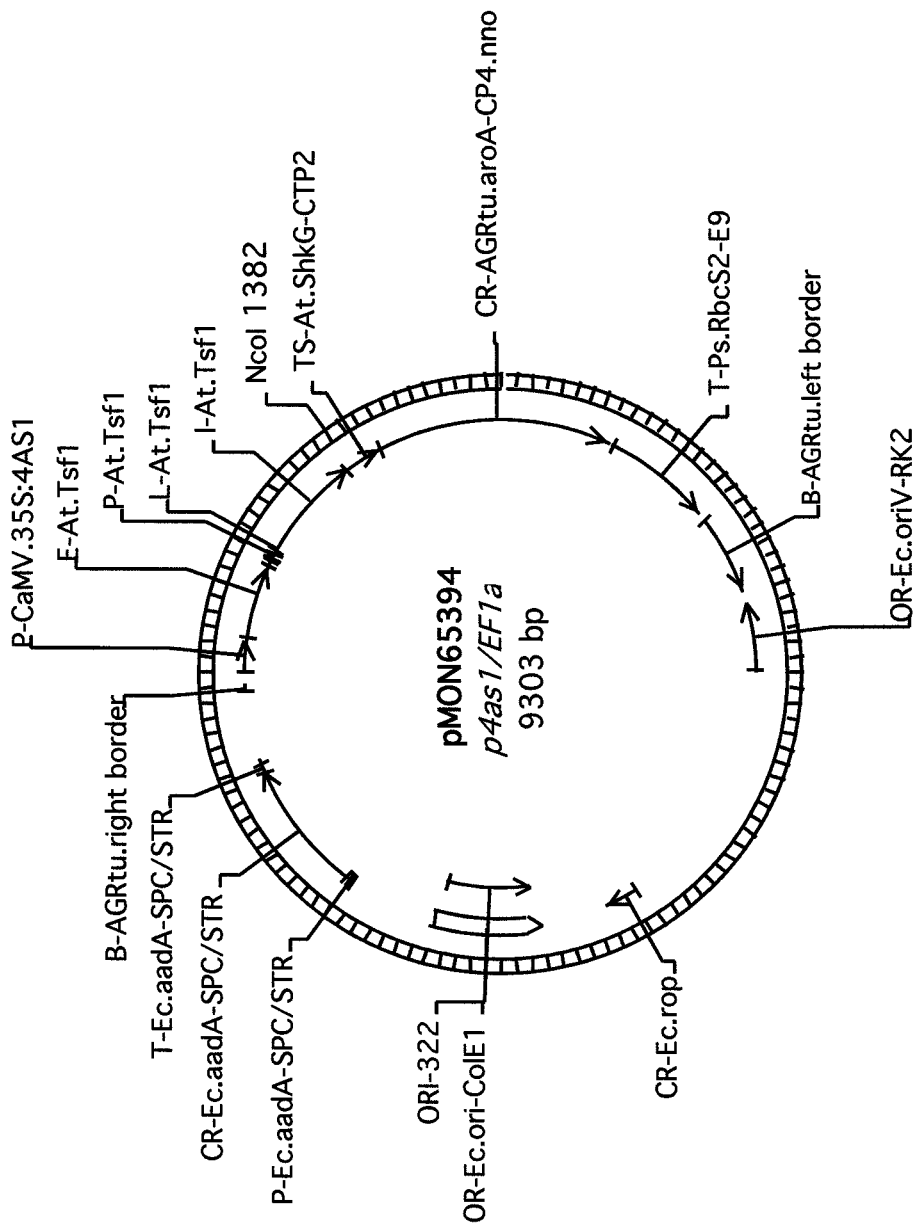
FIG. 11 illustrates the pMON65394 DNA construct, comprising a right border region from *Agrobacterium tumefaciens* (B-AGRtu.right border), a chimeric promoter comprising an promoter enhancer segment (E-CaMV.35S:4as1) from Cauliflower mosaic virus 35S promoter linked to a promoter enhancer segment from *Arabidopsis thaliana* elongation factor 1 alpha gene (E-At.Tsf1) linked to a promoter segment from *Arabidopsis thaliana* elongation factor 1 alpha gene (P-At.Tsf1) linked to a leader segment from *Arabidopsis thaliana* elongation factor 1 alpha gene (L-At.Tsf1) linked to an intron segment from *Arabidopsis thaliana* elongation factor 1 alpha gene (I-At.Tsf1) linked to a transit signal peptide coding sequence from *Arabidopsis thaliana* ShkG (TS-At.ShkG-CTP2), linked to the artificial coding sequence for the glyphosate resistant EPSPS from *Agrobacterium tumefaciens* CP4 (CR-AGRtu.aroA-CP4.nno), linked to a 3' termination region from pea rubisco small subunit (T-Ps.Rbc.S2-E9), linked to a left border region from *Agrobacterium tumefaciens* (B-AGRtu.left border).

SEQ ID NO: 11 is the sequence of the chimeric promoter p4 as 1/AtTsf1 (illustrated as pMON65394 in FIG. 11).

SEQ ID NO: 12 is the sequence of the plant promoter AtTAU2.

SEQ ID NO: 13 is the sequence of the plant promoter NsChslk.

SEQ ID NO: 14 is the sequence of the plant promoter AtP40.

SEQ ID NO: 15 is the sequence of the plant promoter AtTsf1.

SEQ ID NO: 16 is the sequence of the plant promoter NteIF4A10.

SEQ ID NO: 17 is the sequence of the plant promoter AtHsp81-2.

SEQ ID NO: 18 is the sequence of the plant promoter At.STP.

SEQ ID NO: 19 is the FMV enhancer element.

SEQ ID NO: 20 is the CaMV 35S viral enhancer element.

SEQ ID NO: 21 is the CaMV 2XA1B3 viral enhancer element.

SEQ ID NO: 22 is the CaMV 35S:4as1 viral enhancer element.

DETAILED DESCRIPTION OF THE INVENTION

The following definitions and methods are provided to better define the present invention and to guide those of ordinary skill in the art in the practice of the present invention. Unless otherwise noted, terms are to be understood according to conventional usage by those of ordinary skill in the relevant art.

The invention disclosed herein provides novel chimeric promoters. The design, construction, and use of these DNA molecules is one object of this invention. The invention also includes DNA constructs comprising the chimeric promoters; transgenic plant cells, plants, and seeds comprising the chimeric promoters operably linked to a transcribable DNA molecule; and methods of making and using the chimeric promoters, the DNA constructs comprising the chimeric promoters, and the transgenic plant cells, plants, and seeds comprising the chimeric promoters.

DNA Molecules

As used herein, the term "DNA" or "DNA molecule" refers to a double-stranded DNA molecule of genomic or synthetic origin, i.e., a polymer of deoxyribonucleotide bases or a polynucleotide molecule, read from the 5' (upstream) end to the 3' (downstream) end. As used herein, the term "DNA sequence" refers to the nucleotide sequence of a DNA molecule. The nomenclature used herein is that required by Title 37 of the United States Code of Federal Regulations §1.822 and set forth in the tables in WIPO Standard ST.25 (1998), Appendix 2, Tables 1 and 3.

As used herein, the term "isolated DNA molecule" refers to a DNA molecule at least partially separated from other molecules normally associated with it in its native state. In one embodiment, the term "isolated" is also used herein in reference to a DNA molecule that is at least partially separated from nucleic acids which normally flank the DNA molecule in its native state. Thus, DNA molecules fused to regulatory or coding sequences with which they are not normally associated, for example as the result of recombinant techniques, are considered isolated herein. Such molecules are considered isolated even when present, for example in the chromosome of a host cell, or in a nucleic acid solution. The term "isolated" as used herein is intended to encompass molecules not present in their native state.

Any number of methods well known to those skilled in the art can be used to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

As used herein "sequence identity" refers to the extent to which two optimally aligned polynucleotide or polypeptide sequences are identical throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *Journal of Molecular Biology*, 48:443-453 (1970)) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Advances in Applied Mathematics*, 2:482-489, 1981, Smith et al., *Nucleic Acids Research*, 11:2205-2220 (1983)). The percent identity is most preferably determined using the "Best Fit" program.

Useful methods known to those of skill in the art for determining sequence identity are also disclosed in *Guide to Huge Computers*, Martin J. Bishop, ed., Academic Press, San Diego (1994) and Carillo, H., and Lipton, D., *Applied Math.*, 48:1073 (1988). More particularly, preferred computer programs for determining sequence identity include the Basic Local Alignment Search Tool (BLAST) programs, which are publicly available from National Center Biotechnology Information (NCBI) at the National Library of Medicine, National Institute of Health, Bethesda, Md. 20894 (see also, *BLAST Manual*, Altschul et al., NCBI, NLM, NIH and Altschul et al., *Journal of Molecular Biology*, 215:403-410 (1990)). For polynucleotide sequence BLASTN can be used to determine sequence identity, and version 2.0 or higher of BLAST programs allows the introduction of gaps (deletions and insertions) into alignments. In certain aspects, a DNA molecule of the invention is at least about 70, 80, 85, 90, 95, 99 or 99.5 percent identical to a polynucleotide sequence of SEQ ID NO: 1-11. Thus, one embodiment of the invention is a DNA molecule that has at least about 98% sequence identity with a polynucleotide sequence provided as SEQ ID NO: 1-11.

Promoters

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, that is a promoter produced through the fusion of two or more DNA molecules.

Promoters may be characterized by their gene expression pattern, i.e., as constitutive and/or by their temporal, spatial, developmental, tissue, environmental, physiological, pathological, cell cycle, and/or chemically responsive expression pattern, and any combination thereof, as well as by quantitative or qualitative indications. A promoter is useful as a regulatory element for modulating the expression of an operably linked transcribable DNA molecule.

As used herein, a "gene expression pattern" is any pattern of gene expression. The term "gene expression" refers to the transcription of a transcribable DNA molecule into a transcribed RNA molecule. Gene expression may be characterized by its temporal, spatial, developmental, tissue, environmental, physiological, pathological, cell cycle, and/or chemically responsive qualities as well as by quantitative or qualitative indications. The transcribed RNA molecule may be translated to produce a protein molecule or may provide an antisense or other regulatory RNA molecule, such as a dsRNA, a tRNA, an rRNA, a miRNA, and the like.

As used herein, the term "protein expression" refers to the translation of a transcribed RNA molecule into a protein molecule. Protein expression may be characterized by its temporal, spatial, developmental, or morphological qualities as well as by quantitative or qualitative indications.

As used herein, the term "gene regulatory activity" refers to the ability to affect the expression pattern of an operably linked transcribable DNA molecule by affecting the transcription and/or translation of that DNA molecule. Gene regulatory activity may be positive and/or negative and the effect may be characterized by its temporal, spatial, developmental, tissue, environmental, physiological, pathological, cell cycle, and/or chemically responsive qualities as well as by quantitative or qualitative indications.

As used herein, the term "regulatory element" refers to a DNA molecule having gene regulatory activity, i.e., one that has the ability to affect the transcription and/or translation of an operably linked transcribable DNA molecule. Regulatory elements such as promoters, leaders, introns, and transcription termination regions are DNA molecules that have gene regulatory activity and play an integral part in the overall expression of genes in living cells. Isolated regulatory elements, such as promoters, that function in plants are therefore useful for modifying plant phenotypes through the methods of genetic engineering.

A promoter may comprise fragments that have independent promoter activity. Promoter fragments may be useful alone or in combination with other promoters and promoter fragments, such as in constructing chimeric promoters. Fragments of a promoter comprise at least about 50, 95, 150, 250, 500, and 750 contiguous nucleotides of the DNA sequence of the promoter molecule.

A promoter or promoter fragment may also be analyzed for the presence of known promoter elements, i.e., DNA sequence characteristics, such as a TATA-box and other known transcription factor binding site motifs. Identification of such known promoter elements may be used by one of skill in the art to design modified versions of the promoter having a similar expression pattern to the original promoter. Such modified versions of the promoter may be a shorter or truncated version of the original promoter and/or a variant version of the sequence of the original promoter, such as one with different restriction enzyme sites, internal deletions, and/or internal insertions. Such modified versions would usually have the same or similar expression pattern of the original promoter. Production of modified versions of the chimeric promoters of the present invention is well within the ordinary skill of the art and is encompassed within the scope of the present invention.

As used herein, the term "enhancer element" refers to a cis-acting transcriptional regulatory element, a.k.a. cis-element, which confers an aspect of the overall modulation of gene expression. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable DNA molecules are encompassed by the present invention.

An enhancer may comprise fragments that have independent enhancer activity. Enhancer fragments may be useful alone or in combination with other enhancers or promoters or fragments thereof, such as in constructing chimeric promoters. Fragments of an enhancer comprise at least about 50, 95, 150, 250, 500, and 750 contiguous nucleotides of the DNA sequence of the promoter molecule.

A promoter or promoter fragment may comprise one or more enhancer elements that effect the transcription of operably linked genes. Such enhancer elements can be identified using known promoter enhancer elements as a target sequence or target motif in the BLAST programs of the present invention.

As used herein, the term "chimeric" refers to a first DNA molecule fused to a second DNA molecule to produce a single chimeric DNA molecule. As used herein, the term "chimeric promoter" refers to a promoter produced through such manipulation of DNA molecules. A chimeric promoter may combine one or more promoter fragments, such as enhancer elements that can confer or modulate gene expression, fused to a heterologous second promoter or promoter fragment with its own partial or complete regulatory elements. Thus, the design, construction, and use of chimeric promoters according to the methods disclosed herein for modulating the expression of operably linked transcribable DNA molecules are encompassed by the present invention.

As used herein, a "plant promoter" is a promoter isolated from a plant. Plant promoters useful in practicing the present invention are provided as SEQ ID NO: 12-18. Any of these plant promoters can be combined with one or more of the plant viral promoter enhancer elements provided herein as SEQ ID NO: 19-22 to create a chimeric promoter molecule of the present invention. If desired, the chimeric promoter can be analyzed in transformed plant cells or plants as described herein to characterize the expression pattern of the chimeric promoter. Such characterization may be useful to select a chimeric promoter that provides a desirable expression pattern for a gene of agronomic interest.

In certain embodiments a chimeric promoter of the invention is defined as a promoter capable of conferring herbicide tolerance in vegetative and reproduction plant tissues when operably linked to a herbicide tolerance gene and transformed into a plant. For example, a chimeric promoter may be defined as capable of confer glyphosate tolerance to vegetative and reproductive tissues of a transgenic plant transformed with a construct comprising the chimeric promoter operably linked to a glyphosate tolerance gene. In certain aspects, a chimeric, promoter is capable of conferring vegetative and reproductive glyphosate tolerant to a transgenic plant at an application rate of about 24, 52, 96, or 124 oz/Acre of a glyphosate composition (e.g., Roundup® Ultra or Roundup UltraMax II®). For example, a chimeric promoter may be defined as capable of conferring about 5%, 10%, 15%, 25%, 30%, 35%, 40%, 45%, 50%, 55%, 60%, 65% or more reproductive tolerance to glyphosate in a transgenic plant.

Constructs

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e., operably linked. As used herein, the term "vector" means any recombinant polynucleotide construct that may be used for the purpose of transformation, i.e., the introduction of heterologous DNA into a host cell.

As used herein, the term "operably linked" refers to a first molecule joined to a second molecule, wherein the molecules are so arranged that the first molecule affects the function of the second molecule. The two molecules may be part of a single contiguous molecule and may be adjacent. For example, a promoter is operably linked to a transcribable DNA molecule if the promoter modulates transcription of the transcribable DNA molecule of interest in a cell.

The constructs of the present invention are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium tumefaciens* cells, permit the integration of the T-DNA into the genome of a plant cell (see, for example, U.S. Pat. No. 6,603,061, hereby incorporated by reference in its entirety). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404; however, other strains known to those skilled in the art of plant transformation can function in the present invention.

Methods are known in the art for assembling and introducing constructs into a cell in such a manner that the transcribable DNA molecule is transcribed into a functional mRNA molecule that is translated and expressed as a protein product. For the practice of the present invention, conventional compositions and methods for preparing and using constructs and host cells are well known to one skilled in the art, see, for example, *Molecular Cloning: A Laboratory Manual*, $3^{rd}$ edition Volumes 1, 2, and 3 (2000) J. F. Sambrook, D. W. Russell, and N. Irwin, Cold Spring Harbor Laboratory Press. Methods for making recombinant vectors particularly suited to plant transformation include, without limitation, those described in U.S. Pat. Nos. 4,971,908; 4,940,835; 4,769,061; and 4,757,011, all of which are hereby incorporated by reference in their entirety. These types of vectors have also been reviewed in the scientific literature (see, for example, Rodriguez, et al., *Vectors: A Survey of Molecular Cloning Vectors and Their Uses*, Butterworths, Boston, (1988) and Glick, et al., *Methods in Plant Molecular Biology and Biotechnology*, CRC Press, Boca Raton, Fla. (1993)). Typical vectors useful for expression of nucleic acids in higher plants are well known in the art and include vectors derived from the tumor-inducing (Ti) plasmid of *Agrobacterium tumefaciens* (Rogers, et al., *Methods in Enzymology*, 153: 253-277 (1987)). Other recombinant vectors useful for plant transformation, including the pCaMVCN transfer control vector, have also been described in the scientific literature (see, for example, Fromm, et al., *Proc. Natl. Acad. Sci. USA*, 82: 5824-5828 (1985)).

Various regulatory elements may be included in a construct. Any such regulatory elements may be provided in combination with other regulatory elements. Such combinations can be designed or modified to produce desirable regulatory features. Constructs of the present invention would typically comprise one or more regulatory elements operably linked to a transcribable DNA molecule operably linked to a 3' transcription termination molecule.

As used herein, the term "leader" refers to a DNA molecule isolated from the untranslated 5' region (5' UTR) of a genomic copy of a gene and defined generally as a segment between the transcription start site (TSS) and the coding sequence start site. Alternately, leaders may be synthetically produced or manipulated DNA elements. A leader can be used as a 5' regulatory element for modulating expression of an operably linked transcribable DNA molecule. For example, non-translated 5' leaders derived from heat shock protein genes have been demonstrated to enhance gene expression in plants (see, for example, U.S. Pat. Nos. 5,659,122 and 5,362,865, all of which are hereby incorporated by reference). Chimeric promoter molecules of the present invention may optionally comprise a native leader linked to the plant promoter segment for which it is naturally found. This molecule may be replaced with a heterologous leader.

As used herein, the term "intron" refers to a DNA molecule that may be isolated or identified from the genomic copy of a gene and may be defined generally as a region spliced out during mRNA processing prior to translation. Alternately, introns may be synthetically produced or manipulated DNA elements. Introns may themselves contain elements such as cis-elements or enhancer elements that effect the transcription of operably linked genes. An intron may be used as a regulatory element for modulating expression of an operably linked transcribable DNA molecule. A construct may comprise introns. The introns may or may not be heterologous with respect to the transcribable DNA molecule sequence. The transcribable DNA molecule sequence in the recombinant vector may comprise introns. The introns may be heterologous with respect to the transcribable DNA molecule sequence. Examples of introns include the rice actin intron (U.S. Pat. No. 5,641,876, hereby incorporated by reference) and the corn HSP70 intron (U.S. Pat. No. 5,859,347, hereby incorporated by reference).

As used herein, the term "3' transcription termination molecule" or "3' region" refers to a DNA molecule that is used during transcription to produce the 3' untranslated region (3' UTR) of an mRNA molecule. The 3' untranslated region of an mRNA molecule may be generated by specific cleavage and 3' polyadenylation, a.k.a. polyA tail. A 3' transcription termination molecule may be operably linked to and located downstream of a transcribable DNA molecule. A 3' transcription termination molecule may include polynucleotides that provide a polyadenylation signal and other regulatory signals capable of affecting transcription, mRNA processing or gene expression. PolyA tails are thought to function in mRNA stability and in initiation of translation. Examples of 3' transcription termination molecules are the nopaline synthase 3' region (nos 3') (see, Fraley, et al., Proc. Natl. Acad. Sci. USA, 80: 4803-4807 (1983)), wheat hsp17 3' region (T-Ta.Hsp17), pea rubisco small subunit 3' region (T-Ps.RbcS2:E9), cotton E6 3' region (U.S. Pat. No. 6,096,950, hereby incorporated by reference), 3' regions disclosed in WO0011200A2, hereby incorporated by reference), and other 3' regions known in the art that can be used in combination with a transcribable DNA molecule, such as the coixin terminator (U.S. Pat. No. 6,635,806, hereby incorporated by reference).

Constructs and vectors may also include a transit peptide coding sequence that expresses a linked peptide that is useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. Nos. 5,188,642 and 5,728,925, both of which are hereby incorporated by reference. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133, hereby incorporated by reference. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.*, 210:437-442 (1987)) or the *Petunia hybrida* EPSPS CTP (CTP4) (della-Cioppa et al., *Proc. Natl. Acad. Sci. USA*, 83:6873-6877 (1986)) has been show to target heterologous EPSPS protein sequences to chloroplasts in transgenic plants. The production of glyphosate tolerant plants by expression of a fusion protein comprising an amino-terminal CTP with a glyphosate resistant EPSPS enzyme is well known by those skilled in the art (see, for example U.S. Pat. Nos. 5,627,061; 5,633,435; and 5,312,910 and EP 0218571; EP 189707; EP 508909; and EP 924299, all of which are hereby incorporated by reference).

Transcribable DNA Molecules

As used herein, the term "transcribable DNA molecule" refers to any DNA molecule capable of being transcribed into a RNA molecule, including, but not limited to, those having protein coding sequences and sequences useful for gene suppression. A "transgene" comprises a transcribable DNA molecule heterologous to a host cell.

A promoter of the present invention may be operably linked to a transcribable DNA molecule that is heterologous with respect to the promoter molecule. The term "heterologous" refers to the relationship between two or more polynucleotide molecules that are derived from different sources. For example, a promoter is heterologous with respect to a transcribable DNA molecule if such a combination is not normally found in nature. In addition, a particular molecule may be "heterologous" with respect to the cell or organism into which it is inserted (i.e., does not naturally occur in that particular cell or organism).

The transcribable DNA molecule may generally be any DNA molecule for which expression of an RNA transcript is desired. Such expression of an RNA transcript may result in translation of the resulting mRNA molecule and thus protein expression. Alternatively, a transcribable DNA molecule may be designed to ultimately cause decreased expression of a specific gene or protein. This may be accomplished by using a transcribable DNA molecule that is oriented in the antisense direction. One of ordinary skill in the art is familiar with using such antisense technology. Briefly, as the antisense transcribable DNA molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, one embodiment of the invention is a chimeric promoter of the present invention, such as those provided as SEQ ID NO: 1-11, operably linked to a transcribable DNA molecule so as to modulate transcription of the transcribable DNA molecule at a desired level or in a desired pattern upon introduction of said construct into a plant cell. In one embodiment, the transcribable DNA molecule comprises a protein-coding region of a gene, and the chimeric promoter affects the transcription of an RNA molecule that is translated and expressed as a protein product. In another embodiment, the transcribable DNA molecule comprises an antisense region of a gene, and the chimeric promoter affects the transcription of an antisense RNA molecule or other similar inhibitory RNA molecule in order to inhibit expression of a specific RNA molecule of interest in a target host cell.

Genes of Agronomic Interest

Transcribable DNA molecules may be genes of agronomic interest. As used herein, the term "gene of agronomic interest" refers to a transcribable DNA molecule that when expressed in a particular plant tissue, cell, or cell type provides a desirable characteristic associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent such as an antisense or dsRNA molecule targeting a particular gene for suppression. The product of a gene of agronomic interest may act within the plant in order to cause an effect upon the plant physiology or metabolism or may be act as a pesticidal agent in the diet of a pest that feeds on the plant.

In one embodiment of the invention, a chimeric promoter of the present invention is incorporated into a construct such that the chimeric promoter is operably linked to a transcribable DNA molecule that is a gene of agronomic interest. The expression of the gene of agronomic interest is desirable in order to confer an agronomically beneficial trait. A beneficial agronomic trait may be, for example, but not limited to, herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production. Examples of genes of agronomic interest known in the art include those for herbicide resistance (U.S. Pat. Nos. 6,803,501; 6,448,476; 6,248,876; 6,225,114; 6,107,549; 5,866,775; 5,804,425; 5,633,435; and 5,463,175, all of which are hereby incorporated by reference), increased yield (U.S. Pat. Nos. RE38,446; 6,716,474; 6,663,906; 6,476, 295; 6,441,277; 6,423,828; 6,399,330; 6,372,211; 6,235,971; 6,222,098; and 5,716,837, all of which are hereby incorporated by reference), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241, all of which are hereby incorporated by reference), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962, all of which are hereby incorporated by reference), virus resistance (U.S. Pat. Nos. 6,617,496; 6,608,241; 6,015,940; 6,013,864; 5,850,023; and 5,304,730, all of which are hereby incorporated by reference), nematode resistance (U.S. Pat. No. 6,228,992, which is hereby incorporated by reference), bacterial disease resistance (U.S. Pat. No. 5,516,671, which is hereby incorporated by reference), plant growth and development (U.S. Pat. Nos. 6,723,897 and 6,518,488, both of which are hereby incorporated by reference), starch production (U.S. Pat. Nos. 6,538, 181; 6,538,179; 6,538,178; 5,750,876; 6,476,295, all of which are hereby incorporated by reference), modified oils production (U.S. Pat. Nos. 6,444,876; 6,426,447; and 6,380, 462, all of which are hereby incorporated by reference), high oil production (U.S. Pat. Nos. 6,495,739; 5,608,149; 6,483, 008; and 6,476,295, all of which are hereby incorporated by reference), modified fatty acid content (U.S. Pat. Nos. 6,828, 475; 6,822,141; 6,770,465; 6,706,950; 6,660,849; 6,596,538; 6,589,767; 6,537,750; 6,489,461; and 6,459,018, all of which are hereby incorporated by reference), high protein production (U.S. Pat. No. 6,380,466, which is hereby incorporated by reference), fruit ripening (U.S. Pat. No. 5,512,466, which is hereby incorporated by reference), enhanced animal and human nutrition (U.S. Pat. Nos. 6,723,837; 6,653,530; 6,5412,59; 5,985,605; and 6,171,640, all of which are hereby incorporated by reference), biopolymers (U.S. Pat. Nos. RE37,543; 6,228,623; 5,958,745, and 6,946,588, all of which are hereby incorporated by reference), environmental stress resistance (U.S. Pat. No. 6,072,103, which is hereby incorporated by reference), pharmaceutical peptides and secretable peptides (U.S. Pat. Nos. 6,812,379; 6,774,283; 6,140, 075; and 6,080,560, all of which are hereby incorporated by reference), improved processing traits (U.S. Pat. No. 6,476, 295, which is hereby incorporated by reference), improved digestibility (U.S. Pat. No. 6,531,648, which is hereby incorporated by reference) low raffinose (U.S. Pat. No. 6,166,292, which is hereby incorporated by reference), industrial enzyme production (U.S. Pat. No. 5,543,576, which is hereby incorporated by reference), improved flavor (U.S. Pat. No. 6,011,199, which is hereby incorporated by reference), nitrogen fixation (U.S. Pat. No. 5,229,114, which is hereby incorporated by reference), hybrid seed production (U.S. Pat. No. 5,689,041, which is hereby incorporated by reference), fiber production (U.S. Pat. Nos. 6,576,818; 6,271,443; 5,981,834; and 5,869,720, all of which are hereby incorporated by reference) and biofuel production (U.S. Pat. No. 5,998,700, which is hereby incorporated by reference).

Alternatively, a gene of agronomic interest can effect the above mentioned plant characteristic or phenotype by encoding a RNA molecule that causes the targeted inhibition of expression of an endogenous gene, for example via antisense, inhibitory RNA (RNAi), or cosuppression-mediated mechanisms. The RNA could also be a catalytic RNA molecule (i.e., a ribozyme) engineered to cleave a desired endogenous mRNA product. Thus, any transcribable DNA molecule that encodes a transcribed RNA molecule that affects an agronomically important phenotype or morphology change of interest may be useful for the practice of the present invention. Methods are known in the art for constructing and introducing constructs into a cell in such a manner that the transcribable DNA molecule is transcribed into a molecule that is capable of causing gene suppression. For example, posttranscriptional gene suppression using a construct with an antisense oriented transcribable DNA molecule to regulate gene expression in plant cells is disclosed in U.S. Pat. Nos. 5,107, 065 and 5,759,829, both of which are hereby incorporated by reference, and posttranscriptional gene suppression using a construct with a sense-oriented transcribable DNA molecule to regulate gene expression in plants is disclosed in U.S. Pat. Nos. 5,283,184 and 5,231,020, both of which are hereby incorporated by reference. Expression of a transcribable polynucleotide in a plant cell can also be used to suppress plant pests feeding on the plant cell, for example, compositions isolated from coleopteran pests (U.S. Patent Publication No. US20070124836, which is hereby incorporated by reference) and compositions isolated from nematode pests (U.S. Patent Publication No. US20070250947, which is hereby incorporated by reference). Plant pests include, but are not limited to arthropod pests, nematode pests, and fungal or microbial pests. Exemplary transcribable DNA molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule can include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable DNA molecule whose expression, or lack thereof, can be screened for or scored in some way. Marker genes for use in the practice of the present invention include, but are not limited to transcribable DNA molecules encoding β-glucuronidase (GUS described in U.S. Pat. No. 5,599,670, which is hereby incorporated by reference), green fluorescent protein and variants thereof (GFP described in U.S. Pat. Nos. 5,491,084 and 6,146,826, both of which are hereby incorporated by reference), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include, but are not limited to: amino-methyl-phosphonic acid, glyphosate, glufosinate, sulfonylureas, imidazolinones, bromoxynil, delapon, dicamba, cyclohezanedione, protoporphyrinogen oxidase inhibitors, ACCase inhibitors and isoxasflutole herbicides. Transcribable DNA molecules encoding proteins involved in herbicide tolerance are known in the art, and include, but are not limited to, a transcribable DNA molecule encoding 5-enolpyruvylshikimate-3-phosphate synthase (EPSPS for glyphosate tolerance described in U.S. Pat. Nos. 5,627,061; 5,633,435; 6,040,497; and 5,094,945, all of which are hereby incorporated by reference); a transcribable DNA molecule encoding a glyphosate oxidoreductase and a glyphosate-N-acetyl transferase (GOX described in U.S. Pat. No. 5,463,175; GAT described in U.S. Patent publication No. 20030083480, and dicamba monooxygenase U.S. Patent publication No. 20030135879, all of which are hereby incorporated by reference); a transcribable DNA molecule encoding bromoxynil nitrilase (Bxn for Bromoxynil tolerance described in U.S. Pat. No. 4,810,648, which is hereby incorporated by reference); a transcribable DNA molecule encoding phytoene desaturase (crtI) described in Misawa, et al., *Plant Journal*, 4:833-840 (1993) and Misawa, et al., *Plant Journal*, 6:481-489 (1994) for norflurazon tolerance; a transcribable DNA molecule encoding acetohydroxyacid synthase (AHAS, aka ALS) described in Sathasiivan, et al., *Nucl. Acids Res.*, 18:2188-2193 (1990) for tolerance to sulfonylurea herbicides; and the bar gene described in DeBlock, et al., *EMBO Journal*, 6:2513-2519 (1987) for glufosinate and bialaphos tolerance. The chimeric promoter molecules of the present invention can express linked transcribable DNA molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco pathogenesis related proteins also known as tobacco PR-S). Other possible selectable marker genes will be apparent to those of skill in the art.

Cell Transformation

The invention is also directed to a method of producing transformed cells and plants which comprise a chimeric promoter operably linked to a heterologous transcribable DNA molecule.

The term "transformation" refers to the introduction of nucleic acid into a recipient host. As used herein, the term "host" refers to bacteria, fungi, or plant, including any cells, tissue, organs, or progeny of the bacteria, fungi, or plant. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules.

There are many methods for introducing heterologous polynucleic acid molecules into plant cells. The method generally comprises the steps of selecting a suitable host cell, transforming the host cell with a recombinant vector, and obtaining the transformed host cell. Suitable methods include bacterial infection (e.g., *Agrobacterium*), binary bacterial artificial chromosome vectors, direct delivery of DNA (e.g., via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.*, 42: 205 (1991)).

Technology for introduction of a heterologous DNA molecule into cells is well known to those of skill in the art. Methods and materials for transforming plant cells by introducing a plant DNA construct into a plant genome in the practice of this invention can include any of the well-known and demonstrated methods including, but not limited to:

(1) chemical methods (Graham and Van der Eb, *Virology*, 54(2):536-539 (1973) and Zatloukal, et al., *Ann. N.Y. Acad. Sci.*, 660: 136-153 (1992));

(2) physical methods such as microinjection (Capecchi, *Cell*, 22(2):479-488 (1980)), electroporation (Wong and Neumann, *Biochim. Biophys. Res. Commun.*, 107(2):584-587 (1982); Fromm, et al, *Proc. Natl. Acad. Sci. USA*, 82(17): 5824-5828 (1985); U.S. Pat. No. 5,384,253, which is hereby incorporated by reference) particle acceleration (Johnston and Tang, *Methods Cell Biol.*, 43(A):353-365 (1994); Fynan, et al., *Proc. Natl. Acad. Sci. USA*, 90(24):11478-11482 (1993)): and microprojectile bombardment (as illustrated in U.S. Pat. Nos. 5,015,580; 5,550,318; 5,538,880; 6,160,208; 6,399,861; and 6,403,865, all of which are hereby incorporated by reference);

(3) viral vectors (Clapp, *Clin. Perinatol.*, 20(1):155-168 (1993); Lu, et al., *J. Exp. Med.*, 178(6):2089-2096 (1993); Eglitis and Anderson, *Biotechniques*, 6(7):608-614 (1988));

(4) receptor-mediated mechanisms (Curiel et al., *Hum. Gen. Ther.*, 3(2):147-154 (1992) and Wagner, et al., *Proc. Natl. Acad. Sci. USA*, 89(13):6099-6103 (1992);

(5) bacterial mediated mechanisms such as *Agrobacterium*-mediated transformation (as illustrated in U.S. Pat. Nos. 5,824,877; 5,591,616; 5,981,840; and 6,384,301, all of which are hereby incorporated by reference);

(6) direct introduction into pollen by injecting a plant's reproductive organs (Zhou, et al., *Methods in Enzymology*, 101:433, (1983); Hess, *Intern Rev. Cytol.*, 107:367 (1987); Luo, et al., *Plant Mol. Biol. Reporter*, 6:165 (1988); Pena, et al., *Nature*, 325:274 (1987));

(7) protoplast transformation (as illustrated in U.S. Pat. No. 5,508,184, which is hereby incorporated by reference); and (8) injection into immature embryos (Neuhaus, et al., *Theor. Appl. Genet.*, 75:30 (1987)).

Any of the above described methods may be utilized to transform a host cell with one or more chimeric promoters and/or constructs of the present invention. Host cells may be any cell or organism such as a plant cell, algae cell, algae, fungal cell, fungi, bacterial cell, or insect cell. Preferred hosts and transformed cells include cells from: plants, *Aspergillus*, yeasts, insects, bacteria and algae.

Methods for transforming dicotyledonous plants, primarily by use of *Agrobacterium tumefaciens* and obtaining transgenic plants have been published for cotton (U.S. Pat. Nos. 5,004,863; 5,159,135; and 5,518,908); soybean (U.S. Pat. Nos. 5,569,834 and 5,416,011; see also, McCabe, et al., Biotechnolgy, 6:923 (1988) and Christou et al., *Plant Physiol.* 87:671-674 (1988)); *Brassica* (U.S. Pat. No. 5,463,174); peanut (Cheng et al., *Plant Cell Rep.*, 15:653-657 (1996) and McKently et al., *Plant Cell Rep.*, 14:699-703 (1995)); papaya; and pea (Grant et al., *Plant Cell Rep.*, 15:254-258 (1995)).

Transformations of monocotyledon plants using electroporation, particle bombardment, and *Agrobacterium* have also been reported. Transformation and plant regeneration have been achieved in asparagus (Bytebier, et al., *Proc. Natl. Acad. Sci.* (*USA*), 84:5354 (1987); barley (Wan and Lemaux, *Plant Physiol*, 104:37 (1994)); maize (Rhodes, et al., *Science* 240: 204 (1988), Gordon-Kamm, et al., Plant Cell, 2:603-618 (1990), Fromm, et al., *Bio/Technology*, 8:833 (1990), Koziel et al., *Bio/Technology*, 11:194 (1993), and Armstrong, et al., *Crop Science*, 35:550-557 (1995)); oat (Somers, et al., *Bio/Technology*, 10:1589 (1992)); orchard grass (Horn, et al., *Plant Cell Rep.* 7:469 (1988)); rye (De la Pena, et al., *Nature*, 325:274 (1987)); sugarcane (Bower and Birch, *Plant Journal*, 2:409 (1992)); tall fescue (Wang, et al., *Bio/Technology*, 10:691 (1992)); and wheat (Vasil, et al., *Bio/Technology*, 10:667 (1992) and U.S. Pat. No. 5,631,152).

The regeneration, development, and cultivation of plants from transformed plant protoplast or explants is well known in the art (see, for example, Weissbach and Weissbach, *Methods for Plant Molecular Biology*, (Eds.), Academic Press, Inc., San Diego, Calif. (1988) and Horsch et al., *Science*, 227:1229-1231 (1985)). Transformed cells are generally cultured in the presence of a selective media, which selects for the successfully transformed cells and induces the regeneration of plant shoots and roots into intact plants (Fraley, et al., *Proc. Natl. Acad. Sci. U.S.A.*, 80: 4803 (1983)). Transformed plants are typically obtained within two to four months.

The regenerated transgenic plants are self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, *Principles of Plant Breeding*, John Wiley & Sons, NY, U. of CA, Davis, CA, 50-98 (1960); Simmonds, *Principles of crop improvement*, Longman, Inc., NY, 369-399 (1979); Sneep and Hendriksen, Plant breeding perspectives, Wageningen (ed), Center for Agricultural Publishing and Documentation (1979); Fehr, *Soybeans: Improvement, Production and Uses*, 2nd Edition, Monograph., 16:249 (1987); Fehr, *Principles of variety development, Theory and Technique*, (Vol 1) and *Crop Species Soybean* (Vol 2), Iowa State Univ., Macmillian Pub. Co., NY, 360-376 (1987). Conversely, pollen from non-transgenic plants may be used to pollinate the regenerated transgenic plants.

The transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable DNA molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wi) reagents and methods as described by the manufacturer can be used trans gene expression.

The seeds of the plants of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleic acid molecule to its progeny. Progeny includes any regenerable plant part or seed comprising the transgene derived from an ancestor plant. The transgenic plant is preferably homozygous for the transformed polynucleic acid molecule and transmits that sequence to all of it's offspring upon as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immuno-precipitation, and ELISA.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense. Each patent and other reference cited herein is herein is hereby incorporated by reference in its entirety.

EXAMPLES

Plant promoters useful to drive expression of an herbicide tolerance gene in transgenic plants were combined with viral promoter enhancer elements to construct novel chimeric promoters. The expression pattern of these chimeric promoters was then analyzed in transgenic plants.

Example 1

Plant Promoter Molecules

Plant promoters useful to drive expression of a gene in a transgenic plant were identified. To analyze these plant promoters, each promoter was operably linked to the glyphosate tolerance gene for EPSPS (described in U.S. Pat. Nos. 5,627,061; 5,633,435; 6,040,497; and 5,094,945, all of which are hereby incorporated by reference) in a plant transformation vector, which was then used to transform *Arabidopsis thaliana* plants. The resulting transgenic *A. thaliana* plants were then tested for glyphosate tolerance as described in U.S. Publication No. 20040060078 (hereby incorporated by reference). Table 1 provides the results of this analysis for each plant promoter tested. Glyphosate tolerance was measured as the percentage of transgenic *A. thaliana* T1 lines tolerant to glyphosate in vegetative tissues and in reproductive tissues at the equivalent of 24 ounces per acre and 124 ounces per acre, respectively. In Table 1, "NA" indicates not analyzed.

TABLE 1

| Plant Promoter | Vegetative 24 oz/ Acre | Vegetative 124 oz/ Acre | Reproductive 24 oz/ Acre | Reproductive 124 oz/ Acre |
| --- | --- | --- | --- | --- |
| AtP40 | 93 | 81 | 66 | 38 |
| AtTsf1 | 94 | 93 | 64 | 65 |
| AtHsp81-2 | 48 | 34 | 21 | 22 |
| AtTsf1β | 96 | NA | 88 | NA |
| NteIF4A | 82 | 86 | 48 | 34 |
| AtenrA | 94 | 79 | 72 | 51 |
| AtAct7 | 100 | 86 | 89 | 75 |
| AtPK6 | >60 | NA | 60 | NA |
| AtTUA2 | 88 | 79 | 60 | 48 |
| FIB1 | 62 | 68 | 54 | 35 |
| At60S Ribosomal protein-like | 86 | NA | 80 | NA |

TABLE 1-continued

| Plant Promoter | Vegetative 24 oz/ Acre | Vegetative 124 oz/ Acre | Reproductive 24 oz/ Acre | Reproductive 124 oz/ Acre |
| --- | --- | --- | --- | --- |
| AtEndochitinase | 86 | 76 | 57 | 41 |
| AtMRPcp5 | 59 | NA | 36 | NA |
| AtTCTP1 | 81 | 58 | 50 | 23 |

Generally, a high level of both vegetative and reproductive tolerance to glyphosate is desired in transgenic plants for commercial value. Each of the plant promoters when driving expression of EPSPS were able to provide a percentage of T1 lines with vegetative glyphosate tolerance, but only some were able to provide a percentage of T1 lines with glyphosate tolerance in both vegetative and reproductive tissues at the 124 oz/Acre glyphosate treatment rate. Selected plant promoters listed in Table 1 were also tested in transgenic soybean. Vegetative and reproductive glyphosate tolerance was observed in transgenic soybean plants with the AtTsf1, AtP40, and NteIF4A promoters driving the EPSPS gene. Only vegetative glyphosate tolerance was observed with the other selected plant promoters driving the EPSPS in transgenic soybean plants.

From these results, selected plant promoters provided as SEQ ID NO: 12-18 were identified as being of special interest for use in construction of chimeric promoters.

Example 2

Viral Enhancer Elements

Selected enhancer elements from plant virus promoters, referred to herein as viral enhancer elements and provided as SEQ ID NO: 19-22 were identified as being of special interest for use in construction of chimeric promoters.

The FMV viral enhancer element is a promoter enhancer from the 35S transcript of the Figwort mosaic virus (FMV), see U.S. Pat. Nos. 6,051,753 and 6,949,696 hereby incorporated by reference. The FMV enhancer element is provided as SEQ ID NO: 19.

The viral enhancer element e35S is a duplicated promoter enhancer (−350 to −90) from the CaMV 35S promoter, see U.S. Pat. No. 5,424,200 hereby incorporated by reference. The e35S enhancer element is provided as SEQ ID NO: 20.

The viral enhancer element A1-B3 is a promoter enhancer from the 35S promoter of the Cauliflower mosaic virus (CaMV), see U.S. Pat. Nos. 5,097,025 and 7,371,848 hereby incorporated by reference. A duplicated A1-B3 enhancer (herein referred to as 2XA1B3) was constructed with two tandem copies of the A1-B3 enhancer element linked by a five polynucleotide linker. The 2XA1B3 enhancer element is provided as SEQ ID NO: 21.

The p4as1 viral enhancer element is a four tandem repeat of the "activation sequence" (−83 to −62) of the CaMV 35S promoter, see U.S. Pat. No. 7,371,848 hereby incorporated by reference. The p4as1 enhancer element is provided as SEQ ID NO: 22.

Example 3

Construction of Chimeric Promoters

This example describes the construction of novel chimeric promoters useful for expressing transgene in plants by combining viral enhancer elements with plant promoters. These chimeric promoters are provided as SEQ ID NO: 1-11. Techniques used for constructing chimeric DNA molecules and plant transformation vectors are well-known to those of skill in the art of DNA manipulation.

To produce the chimeric promoters AtTsf1/2XA1B3/I-AtTsf1 (provided as SEQ ID NO: 1) and 2XA1B3/AtTsf1 (provided as SEQ ID NO: 10) a base plant transformation vector with an EPSPS gene was made containing the *Arabidopsis thaliana* elongation factor 1 alpha (AtTsf1) promoter (provided as SEQ ID NO: 15). The sequence was modified using standard PCR techniques to create desirable restriction enzyme sites. This base construct was then used to construct a chimeric promoter in which the 2XA1-B3 enhancer element was combined with the AtTsf1α promoter. The 2XA1B3 enhancer DNA fragment was cloned in the desired orientation in the base vector to produce the chimeric promoters. The AtTsf1/2XA1B3/I-AtTsf1 promoter also contains the AtTsf1 intron. The resulting DNA constructs containing the AtTsf1/2XA1B3/I-AtTsf1 and 2XA1B3/AtTsf1/IAtTsf1 promoters are illustrated in FIGS. 1 and 10, respectively.

To produce the chimeric promoter e35S/AtTsf1 (provided as SEQ ID NO: 9), a base plant transformation vector with an EPSPS gene was made containing the *Arabidopsis thaliana* elongation factor 1 alpha (AtTsf1) promoter (provided as SEQ ID NO: 15). The sequence was modified using standard PCR techniques to create desirable restriction enzyme sites. This base construct was then used to construct a chimeric promoter in which the enhancer element of CaMV35S −90 promoter was combined with the AtTsf1 promoter. The enhancer element was cloned in the desired orientation in the base vector to produce the e35S/AtTsf1 chimeric promoter (provided as SEQ ID NO: 9). The resulting DNA construct containing the e35S/AtTsf1 chimeric promoter is illustrated in FIG. 9.

To produce the chimeric promoter p4as1/AtTsf1 (provided as SEQ ID NO: 11), a base plant transformation vector with an EPSPS gene was made containing the *Arabidopsis thaliana* elongation factor 1 alpha (AtTsf1) promoter (provided as SEQ ID NO: 15). The sequence was modified using standard PCR techniques to create desirable restriction enzyme sites. This base construct was then used to construct a chimeric promoter in which the enhancer element p4as1 was combined with the AtTsf1 promoter. The enhancer element was cloned in the desired orientation in the base vector to produce the p4as1/AtTsf1 chimeric promoter (provided as SEQ ID NO: 11). The resulting DNA construct containing the p4as1/AtTsf1 chimeric promoter is illustrated in FIG. 11.

To produce the chimeric promoter FMV/NteIF4A10 (provided as SEQ ID NO: 2), a base plant transformation vector with an EPSPS gene was made containing the *Nicotianum tobaccum* elongation initiation factor 4 A (NteIF4A10) promoter (provided as SEQ ID NO: 16). The sequence was engineered using standard PCR techniques to have desirable restriction enzyme sites. This base construct was then used to construct a chimeric promoter in which enhancer element of FMV promoter was combined with the NteIF4A10 promoter. The enhancer element was cloned in the desired orientation in the base vector to produce the FMV/NteIF4A10 chimeric promoter (provided as SEQ ID NO: 2). The resulting DNA construct is illustrated in FIG. 2.

To produce the chimeric promoter e35S/NteIF4A (provided as SEQ ID NO: 3), a base plant transformation vector with an EPSPS gene was made containing the *Nicotianum tobaccum* elongation initiation factor 4 A (NteIF4A10) promoter (provided as SEQ ID NO: 16). The sequence was engineered using standard PCR techniques to have desirable restriction enzyme sites. This base construct was then used to construct a chimeric promoter in which enhancer element of CaMV35S −90 promoter was combined with the NteIF4A10 promoter. The enhancer element was cloned in the desired orientation in the base vector to produce the e35S/NteIF4A10 chimeric promoter (provided as SEQ ID NO: 3). The resulting DNA construct is illustrated in FIG. 3.

To produce the chimeric promoter FMV/NsChslk/FMV (provided as SEQ ID NO: 4), a base plant transformation vector with an EPSPS gene was made containing the *Nicotiana sylvestris* Chalcone synthase (NsChslk) promoter (provided as SEQ ID NO: 13). The promoter sequence was cloned and engineered using standard PCR techniques to have desirable restriction enzyme sites. This base construct was then used to construct a chimeric promoter in which enhancer element of the FMV promoter was combined with the NsChslk promoter. Two FMV enhancer element DNA fragments were then cloned in the desired orientation into the base vector, with one fragment 5' to the NsChslk promoter and the other fragment 3' to the NsChslk promoter to produce the FMV/NsChslk/FMV chimeric promoter (provided as SEQ ID NO: 4). The resulting DNA construct is illustrated in FIG. 4.

To produce the chimeric promoter FMV/STP (provided as SEQ ID NO: 5), a base plant transformation vector with an EPSPS gene was made containing the *Arabidopsis thaliana* STP promoter (provided as SEQ ID NO: 18). The sequence was engineered using standard PCR techniques to have desirable restriction enzyme sites. This base construct was then used to construct a chimeric promoter in which enhancer element of the FMV promoter was combined with the STP promoter. The enhancer element was cloned in the desired orientation in the base vector to produce the FMV/STP chimeric promoter (provided as SEQ ID NO: 5). The resulting DNA construct is illustrated in FIG. 5.

To produce the chimeric promoter FMV/P40 (provided as SEQ ID NO: 6), a base plant transformation vector with an EPSPS gene was made containing the *Arabidopsis thaliana* P40 promoter (provided as SEQ ID NO: 14). The sequence was engineered using standard PCR techniques to have desirable restriction enzyme sites. This base construct was then used to construct a chimeric promoter in which enhancer element of the FMV promoter was combined with the P40 promoter. The enhancer element was cloned in the desired orientation in the base vector to produce the FMV/P40 chimeric promoter (provided as SEQ ID NO: 6). The resulting DNA construct is illustrated in FIG. 6.

To produce the chimeric promoter FMV/TAU2 (provided as SEQ ID NO: 7), a base plant transformation vector with an EPSPS gene was made containing the *Arabidopsis thaliana* TAU2 promoter (provided as SEQ ID NO: 12). The sequence was engineered using standard PCR techniques to have desirable restriction enzyme sites. This base construct was then used to construct a chimeric promoter in which enhancer element of the FMV promoter was combined with the TAU2 promoter. The enhancer element was cloned in the desired orientation in the base vector to produce the FMV/TAU2 chimeric promoter (provided as SEQ ID NO: 7). The resulting DNA construct is illustrated in FIG. 7.

To produce the chimeric promoter FMV/Hsp81-2 (provided as SEQ ID NO: 8), a base plant transformation vector with an EPSPS gene was made containing the *Arabidopsis thaliana* Hsp81-2 promoter (provided as SEQ ID NO: 17). The sequence was engineered using standard PCR techniques to have desirable restriction enzyme sites. This base construct was then used to construct a chimeric promoter in which enhancer element of the FMV promoter was combined with the TAU2 promoter. The enhancer element was cloned in the desired orientation in the base vector to produce the FMV/

TAU2 chimeric promoter (provided as SEQ ID NO: 8). The resulting DNA construct is illustrated in FIG. 8.

Example 4

Evaluation of Chimeric Promoters in Transgenic Soybean Plants

The chimeric promoters operably linked to the EPSPS gene in plant transformation vectors were used to transform soybean plants in order to evaluate the resulting transgenic plant's tolerance to glyphosate. Soybean plant tissue was transformed using the *Agrobacterium*-mediated soybean transformation method described in U.S. Pat. No. 6,384,301 and U.S. Publication No. US20050005321A1, both of which are hereby incorporated by reference. The resulting transgenic soybean plants were assayed for vegetative glyphosate tolerance as R1 plants and for reproductive tolerance as R2 plants as described Table 2.

The transgenic soybean plants were screened for the glyphosate tolerance trait as described in US 20040060078. R1 soybean plants were first tested for vegetative tolerance to glyphosate. For R1 evaluations, typically 48 seeds per event were planted in pots and allowed to grow to the R1 growth stage. R1 plant tissue was then analyzed by an ELISA designed to detect the EPSPS protein (as described in U.S. Pat. No. 5,627,061 and U.S. Pat. No. RE 39,247, hereby incorporated by reference). This identified positive expressing plants and was used to determine the segregation ratio of the transgene in the population of plants. Plants were then treated with approximately 52 oz/acre of Roundup UltraMax II® (Registered trademark of Monsanto Technology LLC, St. Louis Mo.) herbicide at the V1 stage. Approximately one week post-spray, the plants were evaluated for chlorosis. Other observations and analysis such as emergence, segregation, pod set and timing, plant height, and maturity analysis were conducted at various growth and plant maturity stages. The transgene copy number and zygosity were also assessed. Transgene copy number and zygosity was assayed by quantitative PCR reaction. Quantitative PCR reaction was performed in Real Time PCR system manufactured by Applied Biosystems (Foster City, Calif.). All reagents including custom primers and probes were purchased from Applied Biosystems and were used according to the instructions provided by the manufacturer. Plants that had one copy of the transgene, no vector backbone, and vegetative glyphosate tolerance were advanced to the R2 nursery for evaluation of reproductive tolerance; these plants are referred to as the R2 plants. R2 Plants were then treated 52 oz/acre Roundup UltraMax II®, and those that were morphologically similar to non-treated plants and produced fertile seeds were considered glyphosate tolerant. Glyphosate tolerance was scored for both vegetative and reproductive tissues as the percentage of the EPSPS-expressing plants tested that were glyphosate tolerant. The results of the analysis for each chimeric promoter tested in transgenic soybean plants are provided in Table 2.

TABLE 2

| Construct | SEQ ID NO | Chimeric Promoter | % Vegetative Tolerance (R1) | % Reproductive Tolerance (R2) |
|---|---|---|---|---|
| 45331 | 15 | AtTsf1 | 43 | 3 |
| 65394 | 11 | p4as1/AtTsf1 | 33 | 33 |
| 65388 | 1 | AtTsf1/2XA1B3/I-AtTsf1 | 41 | 25 |
| 65393 | 10 | 2XA1B3/AtTsf1 | 45 | 22 |
| 73666 | 9 | e35S/AtTsf1 | 78 | 67 |
| 73663 | 16 | NteIF4A10 | 40 | 13 |
| 81705 | 2 | FMV/NteIF4A10 | 73 | 47 |
| 81708 | 3 | e35S/NteIF4A10 | 67 | 22 |
| 71500 | 17 | AtHsp81-2 | 23 | 0 |
| 71516 | 8 | FMV/Hsp81-2 | 63 | 25 |
| 10154 |  | FMV | 89 | 0 |
| 73676 | 4 | FMV/NsChslk/FMV | 50 | 50 |
| 70505 | 12 | NsChslk | 0 | 0 |
| 51919 | 5 | FMV/STP | 52 | 0 |
| 45373 | 14 | P40 | 88 | 25 |
| 71514 | 6 | FMV/P40 | 13 | 4 |
| 45374 | 12 | TAU2 | 70 | 0 |
| 71515 | 7 | FMV/TAU2 | 25 | 0 |
| 10154 |  | FMV | 89 | 0 |

Chimeric promoters constructed using the plant promoter AtTsf1 were analyzed for the ability to drive EPSPS expression in soybean plants and provide glyphosate tolerance. The plant promoter AtTsf1 was used as a control for comparison with four different chimeric promoters constructed using the AtTsf1 promoter and three different viral enhancer elements. An increase in reproductive tolerance to glyphosate was achieved with the chimeric promoter constructs relative to the unmodified AtTsf1 promoter construct. The plant promoter AtTsf1 showed 3 percent of lines having reproductive glyphosate tolerance, but all four of the chimeric promoters showed much better tolerance. The chimeric promoters constructed using the AtTsf1 promoter and the p4as1, 2XA1B3, and e35S elements showed increased reproductive tolerance to glyphosate with 22-67 percent of lines having reproductive glyphosate tolerance. Plants comprising chimeric promoters having 2XA1B3 enhancer elements linked to an AtTsf1 promoter demonstrated increased percent reproductive tolerance of 7 to 10 fold over the plant promoter without any decrease in vegetative tolerance.

Chimeric promoters constructed using the plant promoters NteIF4A10, Hsp81-2, and NsChslk were analyzed for the ability to drive EPSPS expression in soybean plants and provide glyphosate tolerance. The plant promoters NteIF4A and HSP81-2 as well as the viral promoter FMV were used as a control for comparison with chimeric promoters. The percent vegetative tolerance was determined in R1 plants from a segregating population that were positive for the transgenic EPSPS by ELISA. The percent reproductive tolerance was determined in R2 plants that were homozygous for the transgene. The results are provided in Table 2.

An increase in reproductive tolerance to glyphosate was achieved with the chimeric promoter constructs relative to the unmodified plant promoters. The plant promoter NteIF4A showed 13 percent of lines having reproductive glyphosate tolerance, but chimeric promoters constructed using this plant promoter showed much better tolerance. The chimeric promoters constructed using the plant promoter NteIF4A10 combined with the FMV or e35S elements showed increased reproductive tolerance to glyphosate with 47 percent and 22 percent of lines having reproductive glyphosate tolerance, respectively. The chimeric promoters FMV/NteIF4A10 and e35S/NteIF4A10 also showed a higher percentage of lines having vegetative glyphosate tolerance than the plant promoter alone.

The plant promoter NsChslk was not sufficient to provide any tolerance to glyphosate and so no transgenic plants were generated with this promoter alone. However, the chimeric promoter constructed using the NsChslk promoter with two FMV elements showed reproductive tolerance to glyphosate with 50 percent of the lines having reproductive glyphosate tolerance.

These results indicate that the some of the chimeric promoters were able to provide much higher reproductive glyphosate tolerance in transgenic plants than plant promoters or the FMV viral promoter alone. However, not all chimeric promoters tested provided the desirable level of reproductive glyphosate tolerance, but are useful for driving expression of a transgene in vegetative tissues. This is a useful activity when expression in reproductive tissues is either not necessary or not desirable.

Example 5

Evaluation of Chimeric Promoters in Transgenic Tobacco Plants

The chimeric promoters operably linked to the EPSPS gene in plant transformation vectors were used to transform tobacco plants in order to evaluate the resulting transgenic plant's tolerance to glyphosate. *Nicotiana tabacum* cv. *Nicotiana samsun* was transformed by using the leaf disc method (Horsch, et al. (1985) Science 227:1229-1231 and Horsch, et al. (1987) Plant Tissue and Cell Culture pp. 317-329, Alan R. Liss, Inc.). Tobacco shoots were rooted in MS media (R0 plants) and then transferred to soil. Tobacco plants were analyzed for glyphosate tolerance at the R0 stage. After 38 days of growth in soil 30 to 35 plants per construct were sprayed with 96 oz/acre Roundup® Ultra (Monsanto Technology LLC, St. Louis Mo.) herbicide. Control plants were sprayed with 0 oz/acre. Plants were scored for vegetative tolerance to glyphosate and for fertility. Plants with vegetative damage were discarded. Plants treated with glyphosate that were morphologically similar to non-treated plants and also produced viable seeds were considered tolerant.

The results of the analysis for each chimeric promoter tested in transgenic tobacco plants are provided in Table 3. Glyphosate tolerance was scored for both vegetative and reproductive tissues as the percentage of the EPSPS-expressing plants tested that were glyphosate tolerant.

TABLE 3

| Construct | Promoter | SEQ ID NO | % R0 Vegetative Tolerance | % R0 Fertile Plants |
| --- | --- | --- | --- | --- |
| 73666 | e35S/AtTsf1 | 9 | 97 | 55 |
| 81705 | FMV/NteIF4A10 | 2 | 87 | 39 |
| 81538 | FMV/Hsp81-2 | 8 | 84 | 45 |
| 73676 | FMV/NsChslk/FMV | 4 | 100 | 25 |
| 81508 | FMV | | 60 | 0 |
| 73663 | NteIF4A10 | 16 | 71 | 6 |

Chimeric promoters constructed using the plant promoters AtTsf1, NteIF4A10, Hsp81-2, and NsChslk were analyzed for the ability to drive EPSPS expression in tobacco plants and provide glyphosate tolerance. The plant promoter NteIF4A10 and the viral promoter FMV were used as a control for comparison with four different chimeric promoters. A increase in reproductive tolerance to glyphosate was achieved with the chimeric promoter constructs relative to the unmodified plant promoter and viral promoter constructs. Vegetative tolerance was also higher in the chimeric promoter plants. The plant promoter NteIF4A10 showed 6 percent of lines having reproductive glyphosate tolerance and the FMV promoter showed none, but all four of the chimeric promoters showed much better tolerance. The chimeric promoters constructed using the AtTsf1 promoter and the e35S element showed 55 percent of R0 plants fertile after glyphosate treatment. The chimeric promoters constructed using the NteIF4A10 promoter and the FMV element showed 39% of R0 plants fertile after glyphosate treatment. The chimeric promoters constructed using the Hsp81-2 promoter and the FMV element showed 45 percent of R0 plants fertile after glyphosate treatment. The chimeric promoters constructed using the NsChslk promoter and two FMV elements showed 25 percent of R0 plants fertile after glyphosate treatment. Vegetative tolerance to glyphosate ranged from 84-100 percent of R0 plants for the chimeric promoters, as compared to 60 percent and 71 percent for FMV and NteIF4A10, respectively.

Having illustrated and described the principles of the present invention, it should be apparent to persons skilled in the art that the invention can be modified in arrangement and detail without departing from such principles. We claim all modifications that are within the spirit and scope of the appended claims. All publications and published patent documents cited in this specification are hereby incorporated by reference to the same extent as if each individual publication or patent application is specifically and individually indicated to be incorporated by reference.

The invention claimed is:

1. A DNA molecule comprising a chimeric promoter having SEQ ID NO: 8.

2. The DNA molecule of claim 1, wherein said chimeric promoter is operably linked to a transcribable DNA molecule.

3. The DNA molecule of claim 2, wherein the transcribable DNA molecule is a sequence of agronomic interest.

4. The DNA molecule of claim 3, wherein the transcribable DNA molecule is a sequence capable of providing herbicide resistance in plants.

5. The DNA molecule of claim 2, wherein the transcribable DNA molecule is a sequence capable of providing plant pest control in plants.

6. A transgenic plant cell stably transformed with a DNA molecule of claim 1, wherein said DNA molecule is operably linked to a transcribable DNA molecule.

7. The transgenic plant cell of claim 6, wherein said transgenic plant cell is a dicotyledonous plant cell.

8. The transgenic plant cell of claim 7, wherein said transgenic plant cell is selected from the group consisting of tobacco plant cell, tomato plant cell, potato plant cell, soybean plant cell, cotton plant cell, canola plant cell, sunflower plant cell, and alfalfa plant cell.

9. A transgenic plant or plant part comprising the DNA molecule of claim 1.

10. A seed produced from the transgenic plant of claim 9, wherein the seed comprises said DNA molecule.

11. A progeny plant of the transgenic plant of claim 9 or a part thereof, wherein the progeny plant comprises said DNA molecule.

12. A method of producing a hybrid plant comprising: a) growing said transgenic plant of claim 9 to a reproductive stage, and b) crossing said transgenic plant with another plant to produce said hybrid plant, wherein said hybrid plant comprises the DNA molecule.

13. A method of generating a plant with a beneficial agronomic trait comprising: a) transforming plant tissue with a DNA molecule of claim 1 operably linked to a transcribable DNA molecule capable of providing said beneficial agronomic trait; b) obtaining transformed plants; and c) selecting a plant with said beneficial agronomic trait.

14. The method of claim 13, further comprising producing a plurality of plants from said plant with said beneficial agronomic trait.

15. The method of claim 13, wherein said plant with said beneficial agronomic trait is selected from the group consisting of wheat, maize, rye, rice, corn, oat, barley, sorghum, millet, tobacco, tomato, potato, soybean, cotton, canola, sunflower and alfalfa, asparagus, avocado, banana, barley, beans, beet, blackberry, blueberry, broccoli, brussel sprouts, cabbage, canola, cantaloupe, carrot, cassaya, cauliflower, celery, cherry, cilantro, cucumber, eggplant, honey dew, jicama, lettuce, leeks, melon, onion, papaya, parsley, pea, peanut, pepper, plum, pomegranate, poplar, potato, pumpkin, quince, radish, raspberry, spinach, squash, strawberry, sugarbeet, sugarcane, sweet potato, tobacco, tomato, watermelon, yams, and zucchini.

16. The method of claim 13, wherein said transcribable DNA molecule capable of providing said beneficial agronomic trait is a gene controlling the phenotype of a trait selected from the group consisting of: herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production.

* * * * *

UNITED STATES PATENT AND TRADEMARK OFFICE
CERTIFICATE OF CORRECTION

PATENT NO. : 8,940,962 B2  
APPLICATION NO. : 13/062694  
DATED : January 27, 2015  
INVENTOR(S) : Stanislaw Flasinski Page 1 of 1

It is certified that error appears in the above-identified patent and that said Letters Patent is hereby corrected as shown below:

In the Claims

Column 56, Line 41, Claim 16, please delete "gene" and please insert --sequences--

Signed and Sealed this
Seventh Day of July, 2015

Michelle K. Lee
*Director of the United States Patent and Trademark Office*

UNITED STATES PATENT AND TRADEMARK OFFICE
CERTIFICATE OF CORRECTION

PATENT NO. : 8,940,962 B2  
APPLICATION NO. : 13/062694  
DATED : January 27, 2015  
INVENTOR(S) : Stanislaw Flasinski Page 1 of 1

It is certified that error appears in the above-identified patent and that said Letters Patent is hereby corrected as shown below:

Claims

Column 55, Line 31, claim 6, please delete "with a DNA", and insert --with the DNA--

Column 55, Line 54, claim 13, please delete "tissue with a", and insert --tissue with the--

Signed and Sealed this  
Thirteenth Day of October, 2015

Michelle K. Lee  
*Director of the United States Patent and Trademark Office*